United States Patent
Sano et al.

(10) Patent No.: US 8,273,236 B2
(45) Date of Patent: Sep. 25, 2012

(54) PROCESS FOR PRODUCING CARBON DIOXIDE SOLUTION, PRODUCTION APPARATUS, AND CARBONATED WATER

(75) Inventors: Yoh Sano, Kyoto (JP); Masahiko Asano, Kamakura (JP); Hitoshi Yagi, Tokyo (JP)

(73) Assignee: Omsi Co., Ltd., Osaka-shi (JP)

( * ) Notice: Subject to any disclaimer, the term of this patent is extended or adjusted under 35 U.S.C. 154(b) by 834 days.

(21) Appl. No.: 12/158,810

(22) PCT Filed: Sep. 22, 2006

(86) PCT No.: PCT/JP2006/318853
§ 371 (c)(1),
(2), (4) Date: Mar. 12, 2009

(87) PCT Pub. No.: WO2007/077654
PCT Pub. Date: Jul. 12, 2007

(65) Prior Publication Data
US 2009/0175960 A1  Jul. 9, 2009

(30) Foreign Application Priority Data
Dec. 28, 2005 (JP) ................... 2005-378465

(51) Int. Cl.
*C25B 1/00* (2006.01)

(52) U.S. Cl. .......... 205/555; 205/58; 205/628; 204/242; 204/433; 424/715; 424/725; 424/729; 424/735; 424/736

(58) Field of Classification Search ................ 205/555, 205/50, 58, 628; 204/194, 242, 555, 556, 204/559, 433; 424/715, 725, 729, 735, 736
See application file for complete search history.

(56) References Cited

U.S. PATENT DOCUMENTS

| 4,670,114 A | 6/1987 | Beer et al. |
| 5,423,454 A * | 6/1995 | Lippman et al. ................. 222/1 |
| 6,780,304 B1 * | 8/2004 | Maget ........................... 205/555 |

FOREIGN PATENT DOCUMENTS

WO  03/101603 A1  12/2003

OTHER PUBLICATIONS

Supplementary European Search Report issued in EP Patent Application 06798241.1 completed Nov. 21, 2008.
Office Action issued in CN Patent Application No. 200680000651.4 dated Mar. 19, 2010 w/partial English translation.
Office Action issued in European Patent Application No. 06798241.3 dated Mar. 6, 2009.
Office Action issued in European Patent Application No. 06798241.3 dated Jul. 31, 2009.
U.S. Appl. No. 11/917,473, filed Dec. 13, 2007, Sano, et al.

* cited by examiner

*Primary Examiner* — In Suk Bullock
*Assistant Examiner* — Timothy G Kingan
(74) *Attorney, Agent, or Firm* — Oblon, Spivak, McClelland, Maier & Neustadt, L.L.P.

(57) ABSTRACT

A first aqueous solution filled in an electrolytic cell (2) is electrolyzed by applying DC voltage between the electrodes 7a and 7b in said electrolytic cell 2, to form an oxidation field short of electrons in said aqueous solution; and then, a second aqueous solution with carboxylic acid dissolved in it is mixed into the first aqueous solution in oxidation field state, so that the first aqueous solution in oxidation field state obtains electrons and is deoxidized, and the carboxylic acid is oxidized, to produce carbonic acid gas in said aqueous solution. Therefore, the present invention can be used to produce carbonic acid gas solution at a low cost easily.

9 Claims, 9 Drawing Sheets

PROCESS FOR PRODUCING CARBON DIOXIDE SOLUTION, PRODUCTION APPARATUS, AND CARBONATED WATER

This application is a 371 of PCT/JP2006/318853 filed Sep. 22, 2006.

FIELD OF THE INVENTION

The present invention relates to a method and an apparatus for producing carbonic acid gas solution, and a carbonated water produced with said method; wherein, said method comprises: electrolyzing an aqueous solution to form an oxidation field short of electrons in the aqueous solution, mixing other aqueous solutions with carboxylic acid dissolved into the aqueous solution in oxidation field state to oxidize the carboxylic acid and thereby obtain the carbonic acid gas solution with micro bubbles of carbonic acid gas dissolved in aqueous solution.

BACKGROUND OF THE INVENTION

Due to the fact that carbonated spring has good thermal insulation effect, it has been utilized in thermal spring baths and so on. It is substantially considered that the thermal insulation effect of carbonated spring is resulted from the dilatation effect of distal blood vessels containing carbonic acid gas, which improves the body environment.

In addition, as carbonic acid gas enters into the body percutaneously, the capillary bed increases and dilates, and thereby the skin blood circulation improves. Therefore, it has good therapeutic effects on degenerative pathological changes of organs and peripheral circulation blockage.

Carbonated spring has been reported in various articles (e.g., see non-patent document 1 and non-patent document 2).

As indicated in non-patent document 1, through repetitive observations by thermal spring doctors in early stage for major direct effects of carbonated spring, Bode of Bad Nauheim observed hyperemic, velutinous, and rubescent skin (1845); Piderit (1836) and Beneke (1859) stated mitigative sense in carbon dioxide bath and rubescent skin on the bathed part; and Goldschieider discussed in 1911 that the rubescent skin stimulated by carbonic acid was possibly caused by movement of blood vessels.

In addition, as indicated in above articles, two impressive direct effects of carbonic acid bath were observed. One effect is that there are numerous water bubbles on the skin; and the other effect is ruddy skin (according to Usui's Ischemic Demarcation theory, the immersed part can be distinguished apparently from the non-immersed part). The water bubbles are numerous carbonic water bubbles, which contact closely with the skin and have effect of "gas brush".

Furthermore, as indicated in non-patent document 2, the minimum concentration of carbonic acid gas required for therapy is 400 mg; however, as indicated in non-patent document 1, ruddy skin occurs when the concentration of carbonic acid gas reaches to 400 mg.

Since carbonated spring has such good effects, people have been developing the producing method of carbonated spring. Wherein, a method was mentioned in patent document 1.

The producing method of carbonated spring mentioned in patent document 1 was: feeding warm water into a carbonic acid gas dissolver with gas dissipation apparatus, releasing carbonic acid gas as bubbles and dissolve the bubbles in the warm water by using the gas dissipation apparatus immersed in the warm water, so as to produce carbonated spring. After the carbonic acid gas is dissolved in the warm water in said carbonic acid gas dissolver under pressure, the obtained carbonated spring is sent to a gas separator to reduce the pressure to normal pressure, the carbonic acid gas volatilizing from the carbonated spring is guided to a compressor for recovery by the gas separator, and the recovered carbonic acid gas is guided to above carbonic acid gas dissolver and dissolved in the warm water.

However, in the producing method of carbonated spring mentioned in patent document 1, a gas dissipation apparatus is required. Above gas dissipation apparatus has a porous part, by which the carbonic acid gas is formed into a large amount of bubbles and is dissolved in the warm water.

In addition, other known gas dissipation apparatuses include: an apparatus with a hollow linear membrane assembly designed to enclose a perforated tube with front part blocked; wherein, the warm water flowing into the perforated tube flows out from the holes on the perforated tube and contacts with the hollow linear membrane, so that the carbonic acid gas injected from the guide port through the hollow part of the hollow linear membrane is dissolved in the warm water.

Accordingly, fine particles (e.g., impurities) in the warm water may block the porous part or the hollow linear membrane of the gas dissipation apparatus; as a result, the gas dissipation apparatus has to be cleaned or replaced frequently, which is very time-consuming.

Furthermore, since carbonic acid gas bomb, gas separator, and compressor, etc. are required, the apparatus is large in size and high in cost.

In addition, since the producing method of carbonated spring of the prior art utilizes a carbonic acid gas bomb to dissolve the pressurized carbonic acid gas in water, the carbonic acid gas not dissolved in water is directly released to the atmosphere uselessly, which deviates from the carbonic acid gas reduction tenet in recent years, and causes adverse effect to the global environment.

A known method of producing carbonic acid gas in aqueous solution without the use of a carbonic acid gas bomb is to utilize a bath agent mixed with a carbonic acid gas generator consisting of carbonate and acid (e.g., see patent document 2).

Patent document 1: Japanese Unexamined Patent Application Publication No. Hei 11-192421

Patent document 2: Japanese Unexamined Patent Application Publication No. 2005-97238

Non-patent document 1: K. L. Schmid., Carbonated Bath (Carbonated Spring), Magazine of Artificial Carbonated Spring Research Association, 1998, 1(1): 005~009.

Non-patent document 2: B. Hartman, M. Pittler, B. Drews, Carbon Dioxide Thermal Spring Recuperation for Arteriolar Blockage Patients: Physiology and Clinic, Magazine of Artificial Carbonated Spring Research Association, 1998, 1(1): 010~016.

SUMMARY OF THE INVENTION

However, for the bath agent mixed with a carbonic acid gas generator consisting of carbonate and acid, the concentration of the carbonic acid gas is about 100 ppm, which is rather not enough to deliver the unique effect of carbonated spring, i.e., numerous water vapor bubbles on skin and ruddy skin.

In view of above problem, in order to dissolve carbonic acid gas in aqueous solution without the use of carbonic acid gas bomb and thereby to obtain a producing method of artificial carbonated spring featured with the effect of numerous water vapor bubbles on skin and ruddy skin, as a result of intensive study, the present inventors have found that, when oxalic acid solution is electrolyzed, carbonic acid gas will be produced from the anode. Therefore, the present inventors have developed a method for dissolving carbonic acid gas in an aqueous solution at a high concentration.

However, the present inventors have also found that, when oxalic acid solution is only electrolyzed, the carbonic acid gas will be directly released to the atmosphere and there will not be enough carbonic acid gas bubbles dissolved in the aqueous solution. In addition, in view that the carbonic acid gas enters into the body percutaneously, the present inventors believe that, the smaller the carbonic acid gas bubble is, the better the effect will be.

In such circumstance, the present invention provides a method and an apparatus for producing a carbonic acid gas solution, and a carbonated water in which carbonic acid gas is dissolved at a high concentration. The method and apparatus of the present invention can dissolve carbonic acid gas in an aqueous solution at a high concentration and obtain unique effects of carbonated spring, i.e., numerous water vapor bubbles on skin and ruddy skin, in a manner completely different to the method of producing carbonated spring by dissolving pressurized carbonic acid gas from a carbonic acid gas bomb in water in the prior art. The method and apparatus of the present invention do not use carbonic acid gas bomb, is friend to environment, and can easily produce a carbonic acid gas solution with micro bubbles of carbonic acid gas dissolved at a low cost (Japanese Patent Application No. 2005-337575).

The patent application is featured with: applying a DC voltage between the electrodes in an electrolytic tank to electrolyze the oxalic acid solution in said electrolytic tank, so as to produce carbonic acid gas; at the same time, applying ultrasonic wave to the oxalic acid solution to form micro bubbles of carbonic acid gas, and dissolving above micro bubbles in the oxalic acid solution.

However, in above patent application, the electrolyzing time required to ionize the oxalic acid solution is quite long, which is a problem to be solved.

To solve above problem, the present inventors carried out intensive study to see whether the electrolysis needs a long time starting from an alkaline aqueous solution; actually, the present inventors found that gas was generated at anode and cathode quickly when the alkaline aqueous solution is electrolyzed.

In view that potassium oxalate is suitable for producing carbonic acid gas, alkaline potassium oxalate aqueous solution is electrolyzed to produce carbonic acid gas; however, after the hands dip into the electrolyzed aqueous solution, no bubble occurs on skin surface and the skin is not ruddy.

To solve above problem, the invention provides a method and an apparatus for producing a carbonic acid gas solution, and a carbonated water in which carbonic acid gas is dissolved at a high concentration. The method and apparatus of the present invention can dissolve carbonic acid gas in an aqueous solution at a high concentration and obtain unique effects of carbonated spring, i.e., numerous water vapor bubbles on skin and ruddy skin, in a manner completely different to the method of producing carbonated spring by dissolving pressurized carbonic acid gas from a carbonic acid gas bomb in water in the prior art. The method and apparatus of the present invention do not use carbonic acid gas bomb, is friend to environment, and can easily produce a carbonic acid gas solution with micro bubbles of carbonic acid gas dissolved at a low cost in a short time.

To attain above object, the invention puts forward the following technical solutions. In the first aspect of the present invention, the method for producing a carbonic acid gas solution of the present invention is characterized that: in an electrolytic cell with electrodes, a first aqueous solution is electrolyzed by applying a DC voltage between the electrodes, to form an oxidation field short of electrons in the aqueous solution; and a second aqueous solution with a carboxylic acid dissolved is mixed into the first aqueous solution in the oxidation field state, so that the first aqueous solution in the oxidation field state obtains electrons and is deoxidized, and the carboxylic acid is oxidized, to produce carbonic acid gas in the aqueous solution.

In the present invention, the first aqueous solution filled in the electrolytic tank is electrolyzed to form a state short of electrons (oxidation field); the second aqueous solution with carboxylic acid dissolved is mixed into the first aqueous solution in oxidation field state short of electrons, an electron donating reaction occurs in the first aqueous solution, so that the carboxylic acid is oxidized, so as to produce carbonic acid gas in the aqueous solution.

For example, as an example of carboxylic acid, the reaction of oxalic acid is as follows:

$$(COOH)_2 \rightarrow 2CO_2 + 2H^+ + 2e^-$$

In the first aqueous solution where the oxidation field is formed by electrolysis, above electron donating reaction facilitates the formation of carbonic acid gas.

In that way, the formation of carbonic acid gas is accelerated, and the carbonic acid gas is dissolved in the aqueous solution; therefore, in the present invention, it is not required to use the gas dissipation device, carbonic acid gas bomb, gas separator, and compressor that are required in the methods for producing carbonated spring in the prior art.

Therefore, carbonic acid gas solution can be produced at a low cost easily.

In addition, in the second aspect of the present invention, the method for producing carbonic acid gas solution of the present invention is characterized in that: in an electrolytic cell with electrodes, a first aqueous solution is electrolyzed by applying a DC voltage between the electrodes, to form an oxidation field short of electrons in the aqueous solution; and a second aqueous solution with carboxylic acid dissolved is mixed with the first aqueous solution in the oxidation field state, so that the first aqueous solution in the oxidation field state obtains electrons from the second aqueous solution with carboxylic acid dissolved and is deoxidized, and the carboxylic acid is oxidized, to produce carbonic acid gas in the aqueous solution.

In the second aspect of the present invention, the first aqueous solution filled in the electrolytic tank is electrolyzed to form a state short of electrons (oxidation field); the first aqueous solution in the state short of electrons (oxidation field) is mixed with the second aqueous solution with carboxylic acid dissolved, so that an electron donating reaction occurs in the mixed aqueous solution and the carboxylic acid is oxidized; as the result, a great deal of carbonic acid gas is produced instantaneously in the aqueous solution.

For example, as an example of carboxylic acid, the reaction of oxalic acid is as follows:

$$(COOH)_2 \rightarrow 2CO_2 + 2H^+ + 2e^-$$

In the mixed aqueous solution produced by mixing the first aqueous solution in oxidation field state and the second aqueous solution with carboxylic acid dissolved, above electron provision reaction can facilitate the formation of carbonic acid gas.

In that way, the formation of carbonic acid gas is accelerated, and the carbonic acid gas is dissolved in the aqueous solution; therefore, in the present invention, it is not required to use the gas dissipation device, carbonic acid gas bomb, gas separator, and compressor that are required in the methods for producing carbonated spring in the prior art.

Therefore, the carbonic acid gas solution can be produced at a low cost easily.

In the method for producing carbonic acid gas solution in the first or second aspect of the present invention, the first aqueous solution is preferably electrolyzed to a pH value of 6 or higher.

If the pH value is 6 or higher, carbonic acid gas will be produced stably; while if the pH value is lower than 6, the carbonic acid gas will be dissolved in the ions, and the concentration of carbonic acid gas will not increase.

That is to say, the following reaction occurs at the anode:

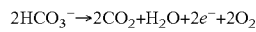

$$2HCO_3^- \rightarrow 2CO_2 + H_2O + 2e^- + 2O_2$$

If the pH value is 6 or higher, above carbonic acid gas will be formed micro bubbles in the electrolyzed solution; while if the pH value is lower than 6, the reverse reaction will occur, and the concentration of carbon dioxide will increase.

Furthermore, in the method for producing carbonic acid gas solution in the first or second aspect of the present invention, after the first aqueous solution is electrolyzed to a pH value of 6 or higher, the second aqueous solution is mixed into the first aqueous solution in the oxidation field state in such an amount that the pH value of the mixed aqueous solution is in a range of 5-7.

According to above method for producing carbonic acid gas solution, after the first aqueous solution is electrolyzed to a pH value of 6 or higher and carbonic acid gas is produced stably, micro carbonic acid gas bubbles exist in the electrolyzed first aqueous solution; then, the second aqueous solution is mixed into the first aqueous solution in the oxidation field state in such an amount that the pH value of the mixed aqueous solution is in a range of 5-7, as the result, micro carbonic acid gas bubbles and carbonic acid gas produced instantaneously by oxidizing carboxylic acid in the first aqueous solution exist in the mixed solution; therefore, the concentration of carbonic acid gas in the mixed solution is increased effectively.

In addition, after the second aqueous solution is added, the mixed solution has a pH value in a range of 5-7 (i.e., in the weakly acidic range); therefore, the solution has mild effect to skin.

In addition, in the method for producing carbonic acid gas solution in the present invention, after the first aqueous solution is electrolyzed to a pH value of 6 or more, an acidic solution is added thereto to adjust the pH value of the first aqueous solution into a range of 5-7, and then, the second aqueous solution is added thereto to keep the pH value within the range of 5-7.

In above method, before the second aqueous solution is added, the pH value in the first aqueous solution is adjusted to 5-7; therefore, it is not required to utilize the second aqueous solution to keep the pH value within 5-7 range, and the generation of carbonic acid gas can be accelerated even if the concentration of the second solution is lowered.

In the third aspect of the present invention, the method for producing carbonic acid gas solution in the present invention is characterized in that: in an electrolytic cell with electrodes, a first aqueous solution is electrolyzed by applying DC voltage between the electrodes to increase the pH value of the first aqueous solution to about 7; whenever the pH value reaches to about 7, an acidic solution that can lower the pH value of the first aqueous solution is added thereto, to prevent the pH value of the first aqueous solution from moving to the alkaline range and to keep the pH value within a weakly acidic range of 6~7, so that an oxidation field short of electrons is formed in the first aqueous solution; and then, a second aqueous solution with carboxylic acid dissolved is mixed into the first aqueous solution in the oxidation field state, so that the first aqueous solution in the oxidation field state obtains electrons and is deoxidized, and the carboxylic acid in the second aqueous solution is oxidized, to produce carbonic acid gas in the aqueous solution.

In the method for producing carbonic acid gas solution in the third aspect of the present invention, whenever the pH value reaches to about 7, an acidic solution that can decrease the pH value is added into the first aqueous solution, to prevent the pH value of the first aqueous solution from moving to the alkaline range and to keep the pH value within a weakly acidic range of 6~7, so as to form an oxidation field short of electrons in the first aqueous solution, which supports stable production of carbonic acid gas for a long time; when the second aqueous solution with carboxylic acid dissolved is mixed into the first aqueous solution in oxidation field state, the first aqueous solution in oxidation field state obtains a great deal electrons and thereby is deoxidized, and the carboxylic acid in the second aqueous solution is oxidized, and thereby further facilitates production of carbonic acid gas in the mixed aqueous solution.

In addition, in the method for producing carbonic acid gas solution in the first or second aspect of the present invention, the first aqueous solution can also be electrolyzed to an oxidation-reduction potential of a negative MV valve.

The oxidation-reduction potential can be used as the reference value for electrolysis in place of the pH value; when the first aqueous solution is electrolyzed to an oxidation-reduction potential of a negative MV valve, an oxidation field short of electrons is formed; then, the second aqueous solution with carboxylic acid dissolved is mixed into the first aqueous solution, so that an electron donating reaction occurs in the mixed aqueous solution, and the carboxylic acid is oxidized; as the result, a great deal of carbonic acid gas is produced instantaneously in the aqueous solution.

In addition, in the method for producing carbonic acid gas solution in the first or second aspect of the present invention, the second aqueous solution can be added after the first aqueous solution is electrolyzed to an oxidation-reduction potential of a negative MV valve.

In above method, after the first aqueous solution is electrolyzed to an oxidation-reduction potential of a negative MV valve and carbonic acid gas is produced stably, micro carbonic acid gas bubbles exist in the electrolyzed first aqueous solution; then, the second aqueous solution is added into the first aqueous solution; therefore, micro carbonic acid gas bubbles and carbonic acid gas produced by oxidizing the carboxylic acid in the second aqueous solution exist in the mixed solution; as the result, the concentration of carbonic acid gas in the mixed aqueous solution is increased effectively.

Furthermore, in any of above methods for producing carbonic acid gas solution in the present invention, it is preferred that carbonate is added into the first aqueous solution before or during the electrolysis.

In above method, after carbonate is added into the first aqueous solution, the carbonate is decomposed, thereby the pH value in the first aqueous solution is increased, and the electrolytic electrolysis is accelerated; in addition, the carbonic acid gas produced in the carbonate reaction and the carbonic acid gas produced by mixing the second aqueous solution in the oxidation field coexist in the mixed solution; as the result, the concentration of carbonic acid gas in the mixed aqueous solution is increased effectively.

In the present invention, said carbonate is preferably sodium bicarbonate. Sodium bicarbonate is soluble in water, and produces sodium ion through the following reaction. The sodium ion combines with carboxylic acid and thereby delivers cushioning effect; therefore, the pH value will not increase.

$NaHCO_3 \rightarrow Na^+ + HCO_3^-$ $-HCO_3^- + H^+ \rightarrow H_2CO_3 \rightarrow CO_2 + H_2O$ In any of above methods for producing carbonic acid gas solution, the first aqueous solution preferably has carboxylic acid and monovalent cation salt of carboxylic acid dissolved.

In the method, since the first aqueous solution has carboxylic acid and monovalent cation salt of carboxylic acid dissolved, the cushioning effect against pH value change in the solution will continue acting even if the electrolysis continues; therefore, stable and safe electrolysis can proceed effectively.

Examples of the monovalent cation are Li, Na, K, Ru, Ce, Fr, etc.

In addition, in any of above methods for producing carbonic acid gas solution, preferably the first aqueous solution is an aqueous solution comprising any one of acidic fruit juice or extract of tea as the major component.

If an aqueous solution comprising any one of acidic fruit juice or extract of tea as the major component is used, the citric acid, malic acid, or tartaric acid in the acidic fruit juice or the oxalic acid in the extract of tea is decomposed, so that carbonic acid gas is produced in the aqueous solution.

The acidic fruit juice can be citrus, shaddock, orange (Balenciaga orange), grapefruit, lemon, sour orange, apple, grape, peach, apricot, cherry, strawberry, pineapple, passion fruit, banana, Japanese apricot, or melon, etc.

When the acidic fruit juice or the extract of tea is used, carbonic acid gas solution can be produced in a safer way.

In any of above methods for producing carbonic acid gas solution, preferably the carboxylic acid is at least one selected from oxalic acid, acetic acid, citric acid, succinic acid, malonic acid, fumaric acid, lactic acid, malic acid, and tartaric acid.

In addition, in any of above methods for producing carbonic acid gas solution, the carboxylic acid dissolved in the second aqueous solution is preferably oxalic acid, citric acid, malic acid, or tartaric acid contained in any of the acidic fruit juice or the extract of tea.

In addition, in the fourth aspect of the present invention, the method for producing carbonic acid gas solution in the present invention is characterized in that, a first aqueous solution comprising any one of acidic fruit juice or extract of tea as the major component and sodium bicarbonate are added into an electrolytic cell with electrodes; the carboxylic acid contained in the fruit juice or tea is electrolyzed by applying a DC voltage between the electrodes in the electrolytic cell, to increase the pH value of the first aqueous solution in the electrolytic cell to 6 or more, and to form an oxidation field short of electrons in the first aqueous solution in the electrolytic cell; and then, a second aqueous solution with carboxylic acid dissolved is mixed into the first aqueous solution in the oxidation field state, and the pH value is kept in the weakly acidic area, so that the first aqueous solution in the oxidation field state obtains electrons and is deoxidized, and the carboxylic acid contained in the second aqueous solution is oxidized, to produce carbonic acid gas in the aqueous solution.

In the fourth aspect of the present invention, the first aqueous solution comprising any one of acidic fruit juice or extract of tea as the major component reacts with sodium bicarbonate to produce carbonic acid gas; in addition, the electrolysis is accelerated by increasing the pH value in the first aqueous solution; the carbonic acid gas produced from carbonate reaction and the carbonic acid gas produced by mixing the second aqueous solution in the oxidation field coexist; as the result, the concentration of carbonic acid gas in the mixed aqueous solution is increased.

In that way, the present invention facilitates the generation of carbonic acid gas, and the carbonic acid gas is dissolved in the aqueous solution; therefore, the present invention does not need gas dissipation device, carbonic acid gas bomb, gas separator, and compressor that are required in the methods for producing carbonated spring of the prior art.

Therefore, in the present invention, carbonic acid gas solution can be produced at a low cost easily.

In addition, in the method for producing carbonic acid gas solution in the fourth aspect, the carboxylic acid dissolved in the second aqueous solution is preferably at least one of oxalic acid, acetic acid, citric acid, succinic acid, malonic acid, fumaric acid, lactic acid, malic acid, and tartaric acid.

Furthermore, in above method for producing carbonic acid gas solution, the carboxylic acid dissolved in the second aqueous solution is preferably oxalic acid, citric acid, malic acid, or tartaric acid contained in any of the acidic fruit juice or the extract of tea.

In addition, in any of above methods for producing carbonic acid gas solution, the first aqueous solution can also be an alkaline aqueous solution.

In above method, the first aqueous solution is prepared into an alkaline aqueous solution to accelerate the electrolysis in it in the electrolytic tank, so that the first aqueous solution forms a state short of electrons (oxidation field) quickly; in the next procedure, when the second aqueous solution with carboxylic acid dissolved is mixed into the first solution, the carboxylic acid will be oxidized quickly, so that a great deal of carbonic acid gas will be produced in the aqueous solution quickly.

In the fifth aspect of the present invention, the method for producing carbonic acid gas solution in the present invention is characterized in that, an alkaline aqueous solution with pH>7 is filled in an electrolytic cell, and is electrolyzed by applying a DC voltage between electrodes in the electrolytic cell to produce hydrogen and oxygen; and after the hydrogen and oxygen are dissolved in the alkaline aqueous solution, an aqueous solution of oxalic acid is added into the alkaline aqueous solution, so that the oxalic acid reacts with the hydrogen and oxygen dissolved in the alkaline aqueous solution, to produce carbonic acid gas solution with micro bubbles of carbonic acid gas dissolved in it.

In the method for producing carbonic acid gas solution in the fifth aspect of the present invention, an alkaline aqueous solution with pH value>7 is electrolyzed to produce hydrogen and oxygen; said hydrogen and oxygen are dissolved in said alkaline aqueous solution; then, oxalic acid aqueous solution is added into the alkaline aqueous solution in oxidation field state resulted from dissolution of hydrogen and oxygen, so that the oxalic acid reacts with the oxygen produced at anode and the hydrogen produced at cathode; and as the result, a great deal of micro carbonic acid gas bubbles are produced instantaneously.

That is to say, through the chemical reaction of hydrogen and oxygen produced during electrolysis in the alkaline aqueous solution with the oxalic acid in the oxalic acid aqueous solution, a great deal of micro bubbles of carbonic acid gas are produced instantaneously.

Therefore, the present invention does not need gas dissipation device, carbonic acid gas bomb, gas separator, or compressor that are required in the method for producing carbonated spring in the prior art. Therefore, the apparatus can easily produce carbonic acid gas solution with micro carbonic acid gas bubbles dissolved at a low cost.

In addition, since the oxalic acid ion in the aqueous solution is ionized in advance; carbonic acid gas solution can be produced in a shorter time.

In the carbonated water (carbonated spring) produced with above method, the hydrogen and oxygen obtained from electrolysis react with the oxalic acid in the oxalic acid aqueous solution to produce micro carbonic acid gas bubbles, and the micro carbonic acid gas bubbles are dissolved in the aqueous solution; therefore, when hands dip into the oxalic acid aqueous solution with micro carbonic acid gas bubbles dissolved, numerous water bubbles will be on skin surface, and the skin will be ruddy.

In above method, it is preferred that the aqueous solution of oxalic acid is added into the alkaline aqueous solution in such an amount that the pH value of the aqueous solution reaches to a weakly acidic area after the aqueous solution of oxalic acid is added thereto.

In above method, since the aqueous solution of oxalic acid is added into the alkaline aqueous solution in such an amount that the pH value of the aqueous solution reaches to a weakly acidic area after the aqueous solution of oxalic acid is added thereto, carbonated water with pH value in the weakly acidic area that is mild to human body skin can be produced; in addition, the concentration of carbonic acid produced with above volume of oxalic acid aqueous solution can deliver the unique effect of numerous water bubbles on skin and ruddy skin, and the appropriate time for producing the carbonated water can be controlled.

In the method for producing carbonic acid gas solution in the fifth aspect of the present invention, the alkaline aqueous solution is preferably produced by dissolving potassium oxalate in water.

In above method, the alkaline aqueous solution is aqueous solution of potassium oxalate; therefore, when the aqueous solution of potassium oxalate is electrolyzed, not only oxygen and hydrogen but also carbonic acid gas are obtained. As a result, carbonated water having a higher concentration can be obtained.

In that case, the reaction mechanism is as follows:

As the potassium oxalate is dissolved in water, the aqueous solution becomes an alkaline aqueous solution. When said alkaline aqueous solution is electrolyzed, hydrogen, oxygen, and carbonic acid gas are produced.

The reaction scheme is as follows:

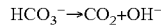

or

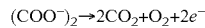

With above reaction scheme, nanometer $CO_2$ particles are produced, and then, the $CO_2$ produced during decomposition of carboxylic acid (e.g., oxalic acid) grows on the existing $CO_2$ nanometer particles (nuclei) into $CO_2$ bubbles.

With above reaction scheme, the oxalic acid added later and the oxalic acid in the oxalic acid aqueous solution in oxidation field state resulted from electrolysis are subjected to reaction, so that a great deal of micro carbonic acid gas bubbles are produced instantaneously.

In the sixth aspect of the present invention, the method for producing carbonic acid gas solution in the present invention is characterized in that, an aqueous solution of potassium oxalate filled in an electrolytic cell is electrolyzed by applying a DC voltage between electrodes in the electrolytic cell to produce carbonic acid gas, hydrogen, and oxygen; and after the carbonic acid gas, hydrogen, and oxygen are dissolved in the aqueous solution of potassium oxalate, an aqueous solution of oxalic acid is added into the aqueous solution of potassium oxalate, to produce carbonic acid gas solution with micro bubbles of carbonic acid gas dissolved in it.

In the method for producing carbonic acid gas solution in the sixth aspect of the present invention, the oxalic acid radical ion in the potassium oxalate aqueous solution is electrolyzed first to produce micro carbonic acid gas bubbles. Then, the aqueous solution of oxalic acid is added into said electrolyzed aqueous solution of potassium oxalate, and the oxalic acid reacts with the oxygen produced at anode and the hydrogen produced at cathode, so that a great deal of micro carbonic acid gas bubbles are produced instantaneously. That is to say, with the micro carbonic acid gas bubbles produced in electrolysis of potassium oxalate aqueous solution and the micro carbonic acid gas bubbles produced in the chemical reaction of the oxalic acid, a great deal of micro carbonic acid gas bubbles are obtained.

Therefore, the present invention does not need gas dissipation device, carbonic acid gas bomb, gas separator, or compressor that are required in the method for producing carbonated spring in the prior art. Therefore, the apparatus can easily produce carbonic acid gas solution with micro carbonic acid gas bubbles dissolved at a low cost.

In addition, since the oxalic acid ion in the aqueous solution is ionized in advance; carbonic acid gas solution can be produced in a shorter time.

In the carbonated water (carbonated spring) produced with above method, the hydrogen and oxygen produced in electrolysis react with the oxalic acid in the aqueous solution of oxalic acid and thereby micro carbonic acid gas bubbles are produced; meanwhile, carbonic acid gas is produced by electrolyzing potassium oxalate; the carbonic acid gas bubbles are dissolved in the aqueous solution; therefore, when hands dip into the oxalic acid aqueous solution with micro bubbles of carbonic acid gas dissolved, the unique effect of numerous water bubbles on skin surface and ruddy skin is obtained.

In the method for producing carbonic acid gas solution in the sixth aspect of the present invention, as the aqueous solution of oxalic acid is added into the electrolyzed aqueous solution of potassium oxalate, the pH value of the aqueous solution of potassium oxalate in the electrolytic cell is measured, in order to control the amount of the aqueous solution of oxalic acid added thereto according to the expected pH value.

In above method, since the aqueous solution of potassium oxalate is strong alkaline, it will be neutralized as the oxalic acid aqueous solution is added; therefore, the amount of oxalic acid aqueous solution added can be controlled according to the expected pH value, to obtain the carbonic acid gas solution having an expected pH value. For example, the addition of the aqueous solution of oxalic acid can be stopped when the pH value of the aqueous solution is in the range of 5.0-6.8, so that weakly acidic carbonic acid gas solution is obtained. Above weakly acidic carbonic acid gas solution is mild to human skin.

In the present invention, ultrasonic wave can be applied to the electrolyzed aqueous solution, so that the carbonic acid gas bubbles will be dissolved in the aqueous solution as smaller bubbles; and therefore, the carbonic acid gas bubbles in the aqueous solution are smaller and more homogeneous.

In the seventh aspect of the present invention, the apparatus for producing carbonic acid gas solution in the present invention characterized in that, as shown in FIG. 1, it is used in the following method for producing carbonic acid gas solution: in an electrolytic cell 2 with electrodes 7a,7b, a first aqueous solution is electrolyzed by applying a DC voltage between the electrodes 7a,7b, to form an oxidation field short of electrons in the aqueous solution; and a second aqueous solution with carboxylic acid dissolved is mixed into the first aqueous solution in the oxidation field state, so that the first aqueous solution in the oxidation field state obtains electrons and is deoxidized, and the carboxylic acid is oxidized, to produce carbonic acid gas in the aqueous solution, wherein a tester 11 is provided in the electrolytic cell 2 to measure any one or the combination of pH value and oxidation-reduction potential.

In the apparatus for producing carbonic acid gas solution in the seventh aspect of the present invention, there is a tester 11 that measures any one or the combination of pH value and oxidation-reduction potential in the electrolytic tank 2 filled with alkaline aqueous solution having a pH value>7, and the apparatus does not need gas dissipation device, carbonic acid gas bomb, gas separator, or compressor, etc. that are required in the method for producing carbonated spring in the prior art.

Therefore, the apparatus can easily produce carbonic acid gas solution with micro carbonic acid gas bubbles dissolved at a low cost.

With the tester 11 that measures any one or the combination of pH value and oxidation-reduction potential in the electrolytic tank 2, the pH value can be controlled and the addition of oxalic acid aqueous solution can be stopped as required, so as to obtain carbonic acid gas solution having the required pH value. For example, the addition of oxalic acid aqueous solution can be stopped when the pH value is in the range of 5.0-6.8, so that a weakly acidic carbonic acid gas solution is obtained.

That is to say, in the electrolytic tank 2 with electrodes 7a and 7b, the first aqueous solution is electrolyzed by applying DC voltage between the electrodes 7a and 7b in the electrolytic tank 2, to form an oxidation field short of electrons in said aqueous solution and the first aqueous solution becomes alkaline. The pH value or oxidation-reduction potential is measured with tester 11, and when the pH value is 5-6.8, the addition of oxalic acid aqueous solution is stopped, so as to obtain the weakly acidic carbonic acid gas solution.

As shown in FIG. 5, the apparatus for producing carbonic acid gas solution in the eighth aspect of the present invention comprises: an electrolytic cell 2A with electrodes 7a,7b; an electrolytic device 3A, which applies a DC voltage on electrodes 7a,7b in the electrolytic cell 2A to electrolyze an aqueous solution in the electrolytic cell 2A; a filling container 50, which is filled with an aqueous solution with carboxylic acid dissolved; a tester 11, which is provided in the electrolytic cell 2A to measure any one or the combination of pH value or oxidation-reduction potential; a controller 3A, which adds the aqueous solution with carboxylic acid dissolved in the filling container 50 into the electrolytic cell 2A when the pH value measured by the tester 11 is ≧7 or the oxidation-reduction potential measured by the tester 11 is a negative MV value.

The apparatus for producing carbonic acid gas solution in the eighth aspect of the present invention mainly comprises: an electrolytic cell 2A with electrodes 7a,7b; an electrolytic device 3A, which applies a DC voltage on electrodes 7a,7b in the electrolytic cell 2A to electrolyze an aqueous solution in the electrolytic cell 2A; a filling container 50, which is filled with an aqueous solution with carboxylic acid dissolved; a tester 11, which is provided in the electrolytic cell 2A to measure any one or the combination of pH value or oxidation-reduction potential; a controller 3A, which adds the aqueous solution with carboxylic acid dissolved in the filling container 50 into the electrolytic cell 2A when the pH value measured by the tester 11 is ≧7 or the oxidation-reduction potential measured by the tester 11 is a negative MV value. Therefore, the apparatus does not need the gas dissipation device, carbonic acid gas bomb, gas separator, or compressor, etc., which are required in the method for producing carbonated spring in the prior art.

Therefore, the apparatus can easily produce carbonic acid gas solution with micro carbonic acid gas bubbles dissolved at a low cost.

In the present invention, the aqueous solution filled in the electrolytic tank 2A is electrolyzed with the electrolytic device 3A, and the pH value or oxidation-reduction potential is measured with the tester 11; therefore, the aqueous solution can be controlled in the appropriate oxidation field state.

Carbonated spring can be produced easily by controlling the addition of the aqueous solution of carboxylic acid in the filling container 50 into the electrolytic tank 2A with the controller 3A.

The apparatus for producing carbonic acid gas solution in the ninth aspect of the present invention is characterized in that: as shown in FIG. 5, it is used in the following method for producing carbonic acid gas solution: a first aqueous solution is electrolyzed to form an oxidation field short of electrons in the aqueous solution; and a second aqueous solution with carboxylic acid dissolved is mixed into the first aqueous solution in the oxidation field state, so that the first aqueous solution in the oxidation field state obtains electrons and is deoxidized, and the carboxylic acid is oxidized, to produce carbonic acid gas in the aqueous solution;

wherein the apparatus for producing carbonic acid gas solution comprises: an electrolytic cell 2A designed to electrolyze the first aqueous solution; electrodes 7a,7b in the electrolytic cell; an electrolytic device 3A, which applies a DC voltage on the electrodes 7a,7b to electrolyze the first aqueous solution in the electrolytic cell 2A; a filling container 50, which is filled with the second aqueous solution with carboxylic acid dissolved in it; a tester 11, which measures any one or the combination of pH value and oxidation-reduction potential of the electrolyzed aqueous solution in the electrolytic cell 2A; a controller 3A, which adds the aqueous solution with carboxylic acid dissolved in said filling container 50 into said electrolytic cell 2A when the pH value measured by the tester 11 is ≧7 or the oxidation-reduction potential measured by the tester 11 is a negative MV value; a reaction vessel 51, in which the first aqueous solution electrolyzed in the electrolytic cell 2A reacts with the second aqueous solution; and a circulating pump 52, which is located between the electrolytic cell 2A and the reaction vessel 51, and circulates the aqueous solution between the electrolytic cell and the reaction vessel.

In the apparatus in the ninth aspect of the present invention, the circulating pump 52 allows the first aqueous solution in electrolytic tank 2A to circulate between the reaction vessel 51 and the electrolytic tank 2A; therefore, predetermined volume of aqueous solution flows into electrolytic tank 2A continuously, so that a great deal of aqueous solution is effectively electrolyzed. Therefore, the efficiency of electrolysis of the aqueous solution is improved. In addition, the circulating aqueous solution is stored in reaction vessel 51 temporarily, and when the second aqueous solution flows out from the filling container 50, the first aqueous solution and the second aqueous solution react in said reaction vessel 51 and thereby a great deal of carbonic acid gas instantaneously is produced in said reaction vessel 51.

Such an apparatus for producing carbonic acid gas solution does not need the gas dissipation device, carbonic acid gas bomb, gas separator, or compressor, etc., which are required in the method for producing carbonated spring in the prior art. Therefore, the apparatus can easily produce carbonic acid gas solution with micro carbonic acid gas bubbles dissolved at a low cost.

In said apparatus in the ninth aspect of the present invention, said reaction vessel 51 is preferably a bath vessel.

If said reaction vessel 51 is a bath vessel, the apparatus is applicable to bathrooms in ordinary residential buildings.

In the tenth aspect of the present invention, the carbonated water is as follows: a first aqueous solution is electrolyzed to form an oxidation field short of electrons in said aqueous solution; and a second aqueous solution with carboxylic acid dissolved in it is mixed into the first aqueous solution in the oxidation field state, so that the first aqueous solution in the oxidation field state obtains electrons and is deoxidized, and the carboxylic acid is oxidized, to produce the carbonated water having an aqueous solution with micro bubbles of carbonic acid gas dissolved as the major component. Above carbonated water, in which micro carbonic acid gas bubbles are dissolved in aqueous solution by oxidizing carboxylic acid, can deliver the unique effect of carbonated spring, i.e., numerous water bubbles on skin surface and ruddy skin, and facilitate the increase and dilatation of capillary bed, and improved blood circulation in skin.

In addition, in the carbonated water in the present invention, the first aqueous solution is preferably an aqueous solution with carboxylic acid dissolved. If the first aqueous solution is an aqueous solution with carboxylic acid dissolved, micro carbonic acid gas bubbles can produced by electrolyzing the first aqueous solution; then, the carbonic acid gas bubbles produced in decomposition of carboxylic acid (e.g., oxalic acid) grow on said micro carbonic acid gas bubbles (nuclei), so as to obtain the unique effect of carbonated spring.

In the carbonated water in the present invention, the first aqueous solution is preferably an aqueous solution with carboxylic acid and monovalent cation salt thereof dissolved in it.

If the first aqueous solution is an aqueous solution with carboxylic acid and monovalent cation salt thereof dissolved in it, said aqueous solution itself serves as buffer solution; therefore, even if the first aqueous solution is electrolyzed, the pH value will not move to the strong alkaline range; as a result, the neutral carbonated water can deliver the unique effect of numerous water bubbles on skin surface and ruddy skin, and facilitate the increase and dilatation of capillary bed, and improved blood circulation in skin.

In addition, in the present invention, the first aqueous solution can also be an aqueous solution comprising any one of acidic fruit juice or extract of tea as the major component.

Carboxylic acid is contained in the acidic fruit juice or extract of tea, to produce a carbonated water that is friendly to the environment and safe to human body.

In the carbonated water of the present invention, the carboxylic acid is preferably at least one selected from oxalic acid, acetic acid, citric acid, succinic acid, malonic acid, fumaric acid, lactic acid, malic acid, and tartaric acid, so that the carbonated water is safe to the environment and human body.

In addition, in the carbonated water in the present invention, the carboxylic acid dissolved in the second aqueous solution is preferably oxalic acid, citric acid, malic acid, or tartaric acid contained in any one of acidic fruit juice or extract of tea, so that the second aqueous solution will be the carbonated water safe to the environment and human body as the first aqueous solution.

In the eleventh aspect of the present invention, the carbonated water is as follows: a first aqueous solution comprising any one of acidic fruit juice or extract of tea as the major component and sodium bicarbonate are added into an electrolytic cell with electrodes; the carboxylic acid contained in the fruit juice or the extract of tea is electrolyzed by applying a DC voltage between the electrodes in the electrolytic cell, till the pH value in the first aqueous solution in the electrolytic tank is about 7 or more, to form an oxidation field short of electrons in the first aqueous solution in the electrolytic cell; and then, a second aqueous solution with carboxylic acid dissolved is mixed into the first aqueous solution in the oxidation field state, and the pH value of the mixed solution is kept in the weakly acidic area, so that the first aqueous solution in the oxidation field state obtains electrons and is deoxidized, and the carboxylic acid in the second aqueous solution is oxidized, to produce the carbonated water having an aqueous solution with micro bubbles carbonic acid gas dissolved as the major component.

Above carbonated water, which is obtained by electrolyzing the aqueous solution comprising any one of acidic fruit juice or extract of tea as the major component to form an oxidation field and then decomposing the carboxylic acid in said oxidation field, is a carbonated water safe to the environment and human body.

In the twelfth aspect of the present invention, the carbonated water is as follows: an aqueous solution of potassium oxalate filled in an electrolytic cell is electrolyzed by applying a DC voltage between electrodes in the electrolytic cell, to produce carbonic acid gas, hydrogen, and oxygen; and after the carbonic acid gas and oxygen are dissolved in the aqueous solution of potassium oxalate, an aqueous solution of oxalic acid is added into the aqueous solution of potassium oxalate, to obtain the carbonated water having an aqueous solution of oxalic acid with micro bubbles carbonic acid gas dissolved as the major component.

Above carbonated water comprising the aqueous solution of oxalic acid with a great deal of micro carbonic acid gas bubbles dissolved in it as the major component, which is obtained by electrolyzing the aqueous solution of potassium oxalate in an electrolytic cell to produce carbonic acid gas, hydrogen and oxygen and then adding the aqueous solution of oxalic acid into said aqueous solution of potassium oxalate after the carbonic acid gas and oxygen are dissolved in said aqueous solution of potassium oxalate, can delivery the unique effect of carbonated spring (numerous water vapor bubbles on skin and ruddy skin), and can facilitate the capillary bed to increase and dilate, so as to improve skin blood circulation.

In any of above carbonated water, if the concentration of carbonated water is $\geqq 400$ ppm, the carbonated water can deliver unique feature of carbonated spring (i.e., numerous water bubbles on skin surface and ruddy skin), and can facilitate increase and dilatation of capillary bed and improve blood circulation in skin.

However, if the concentration is lower than 400 ppm, the carbonated water can not deliver above unique effect. Therefore, by controlling the concentration of carbonated water to be greater than or equal to 400 ppm, required carbonated water having the aqueous solution of oxalic acid with micro carbonic acid gas bubbles dissolved in a certain particle size as the main component can be obtained.

The present invention provide a method that can be used to dissolve high concentration of carbonic acid gas in aqueous solution, which can deliver the unique effect of carbonated spring (i.e., numerous water bubbles on skin surface and ruddy skin); therefore, it is completely different to the method for producing carbonated spring in the prior art that requires pressurization with a carbonic acid gas bomb to make the carbonic acid gas dissolution dissolved in water, and the present invention does not need any gas dissipation device, carbonic acid gas bomb, gas separator, or compressor, etc.

The present invention can be used to produce carbonic acid gas solution with micro carbonic acid gas bubbles dissolved quickly at a low cost, without using carbonic acid gas bomb; in addition, the present invention does not emit unneeded carbonic acid gas to the atmosphere, and therefore is friendly to the environment.

In the method provided in the present invention, in an electrolytic tank with electrodes, the first aqueous solution is electrolyzed by applying DC voltage between the electrodes to form an oxidation field short of electrons; then, the second aqueous solution with carboxylic acid dissolved is mixed into the first aqueous solution in oxidation field state, so that the first aqueous solution in oxidation field state obtains electrons from the second aqueous solution with carboxylic acid and thereby is deoxidized, and the carboxylic acid is oxidized; as a result, carbonic acid gas is produced in the aqueous solution; therefore, the method can be used to produce carbonic acid gas solution with micro carbonic acid gas bubbles dissolved quickly at a low cost, and will not emit unneeded carbonic acid gas to the atmosphere, and thereby is friendly to the environment.

In addition, since the carboxylic acid is decomposed through chemical reaction and the carbonic acid gas is dissolved in the aqueous solution, the carbonated water produced with above method can dissolve micro carbonic acid gas bubbles. So that it can be used to produce carbonated spring that can facilitate the increase and dilatation of capillary bed and the improved blood circulation in skin.

The carbonated water having the aqueous solution of oxalic acid with the micro carbonic acid gas bubbles dissolved as the major component which is produced by above method can deliver the unique effect of carbonated spring (i.e., numerous water bubbles on skin surface and ruddy skin), and can facilitate the increase and dilatation of capillary bed and the improved blood circulation in skin.

BRIEF DESCRIPTION OF THE REFERENCE SIGNS

Figure 1:
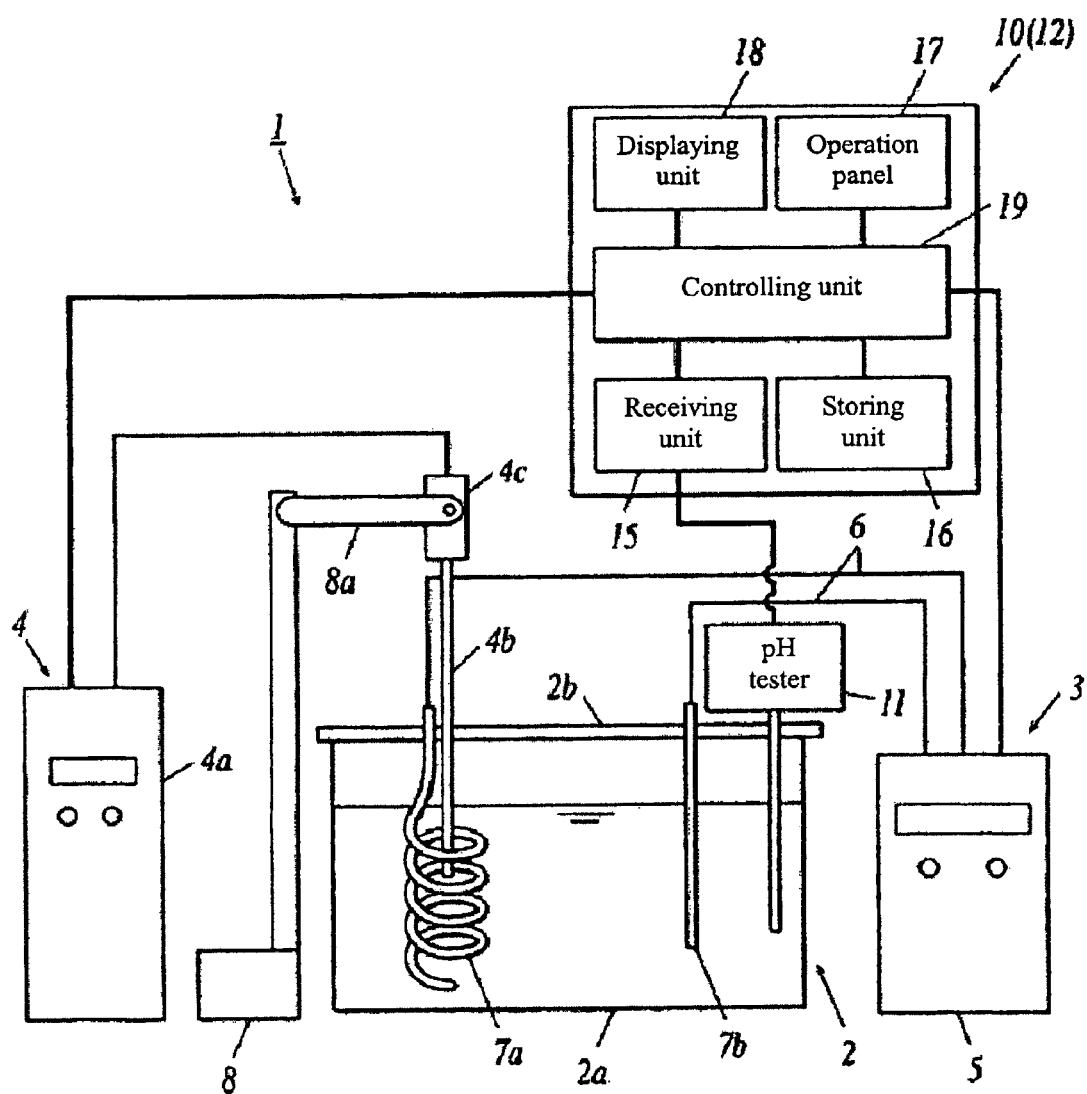
FIG. 1 is a schematic view of the structure of the apparatus for producing carbonic acid gas solution in the invention.

1: Apparatus for producing carbonic acid gas solution
2: Electrolytic cell
2a: Main body of the electrolytic cell
2b: Cover
3: Electrolytic device
4: Ultrasonic generator
4a: Main body of the apparatus
4b: Ultrasonic oscillator
4c: Supporting part
5: Power supply unit
6: Leads
7a, 7b: Electrode
8: Supporting base
8a: Mounting part
10, 12: Operation controller
11: pH tester
15: Receiving unit
16: Storing unit
17: Operation panel
18: Displaying unit
19: Controlling unit
21: Apparatus for producing carbonic acid gas solution
22: Base
22a: Support
22b: Arm
25, 26: Electrode group
25a, 25b, 26a, 26b: Electrode
28: Conductor
40: Apparatus for producing carbonic acid gas solution
50: Filling container
2A: Electrolytic cell
3A: Electrolytic device
3B, 3C, 3D, 3E, 3F: Signal wire
51: Reaction vessel
52: Circulating pump
53: Flow meter
54, 55: Regulating valve
56: Valve
57, 58, 59: Pipeline
60: Outlet pipe
100: Measuring device
200, 210, 220, 230, 240, 250: Container
300, 310, 320, 330, 340, 350: Cover
400, 410, 420, 430, 440, 450, 500, 510, 520, 530, 540, 550: Pipe
610, 620, 630, 640, 650: Connecting pipe

DETAILED DESCRIPTION OF THE EMBODIMENTS

Hereunder the invention will be described in the embodiments, with reference to the accompanying drawings.

First, the raw aqueous solution that is used as the raw material for carbonic acid gas solution will be described. The raw aqueous solution includes: the first aqueous solution to be electrolyzed, and the second aqueous solution to be mixed into the first aqueous solution that is in oxidation field state short of electrons resulted from electrolysis. The raw aqueous solution can be an aqueous solution comprising any one of acidic fruit juice or extract of tea as the major component.

In addition, the first aqueous solution can be an aqueous solution with carboxylic acid dissolved in it. In that case, the carboxylic acid in the first aqueous solution and the second aqueous solution can be at least one selected from oxalic acid, acetic acid, citric acid, succinic acid, malonic acid, fumaric acid, lactic acid, malic acid, and tartaric acid.

For an aqueous solution comprising any one of acidic fruit juice or extract of tea as the major component, the citric acid, malic acid, or tartaric acid in the acidic fruit juice or the oxalic acid in the extract of tea is decomposed, so that carbonic acid gas is produced in the aqueous solution.

Here, examples of the acidic fruit juice include citrus, shaddock, orange (Valencia orange), grapefruit, lemon, sour orange, apple, grape, peach, apricot, cherry, strawberry, pineapple, passion fruit, banana, Japanese apricot, melon, etc.

Those natural juices contain the following amount of citric acid, malic acid, or tartaric acid (with reference to the latest Dictionary of Fruit Juices & Fruit Beverages, supervised by Fruit Juice Association of Japan, Issued by ASAKURA Bookstore, Oct. 1, 1997, Vol. 1).

That is to say, 0.96% citric acid and 0.05% malic acid in citrus (Wenzhou citrus); 1.96% citric acid and 0.05% malic acid in shaddock; 0.98% citric acid in orange (Valencia orange); 1.33% citric acid and 0.08% malic acid in grapefruit; 6.08% citric acid and 0.08% malic acid in lemon; 6.9% citric acid in sour orange; 0.02% citric acid and 0.51% malic acid in apple (Ralls); 0.65% malic acid and 0.43% tartaric acid in grape (コンコード), 0.63% malic acid in peach juicy peach); 1.64% malic acid in apricot; 0.67% malic acid in cherry (Napoleon); 0.91% citric acid and 0.1% malic acid in strawberry; 0.84% citric acid and 0.12% malic acid in pineapple; 2.14% citric acid in passion fruit; 0.32% citric acid and 0.37% malic acid in banana; 3.3% citric acid and 1.1% malic acid in Japanese apricot; 0.1% citric acid and 0.01% malic acid in melon.

Since the first aqueous solution has carboxylic acid and monovalent cation salt of carboxylic acid dissolved, the cushioning effect against pH value change in the solution will continue acting even if the electrolysis continues; therefore, stable and safe electrolysis can be carried out effectively.

The carboxylic acid can be oxalic acid, acetic acid, citric acid, succinic acid, malonic acid, fumaric acid, lactic acid, malic acid, or tartaric acid, etc.

The monovalent cation can be Li, Na, K, Ru, Ce, Fr, etc.

Specifically, examples include combination of oxalic acid and potassium oxalate, acetic acid and sodium acetate, citric acid and sodium citrate, succinic acid and sodium succinate, malonic acid and sodium malonate, fumaric acid and sodium fumarate, lactic acid and sodium lactate, malic acid and sodium malate, or tartaric acid and sodium tartrate, etc.

In addition, the combinations of the buffer solution are not limited to above examples; any combination can be used in the present invention, as long as the solution can minimize the change of its pH value when acid or alkali is added into it.

Furthermore, as the raw aqueous solution, the first aqueous solution can be an alkaline aqueous solution with pH value >7, and in example an aqueous solution with potassium oxalate ($K_2C_2O_4$) dissolved in it is used. In this embodiment, potassium oxalate is used to prepare the alkaline aqueous solution; however, the present invention is not limited to potassium oxalate.

In addition, when the aqueous solution of potassium oxalate is used, potassium oxalate is ionized into oxalic acid radical ion and potassium ion, as shown in the following equation:

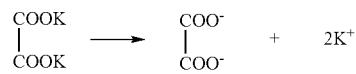

$COO^-$ is the raw material for carbonic acid gas; when the raw aqueous solution is electrolyzed, the following electrochemical reaction occurs at the anode, and carbonic acid gas bubbles are produced:

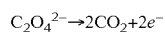

In addition, as an example of carboxylic acid, the reaction of oxalic acid is as follows:

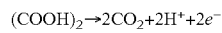

The electrolysis of such raw aqueous solution is carried out by using the apparatus for producing the carbonic acid gas solution as shown in FIG. 1.

Hereunder the case of potassium oxalate aqueous solution used as the first aqueous solution will be described.

The apparatus 1 for producing the carbonic acid gas solution shown in FIG. 1 comprises: electrolytic cell 2 filled with the aqueous solution of potassium oxalate; electrolytic device 3, ultrasonic generator 4, operation controller 10 (12) that control said electrolyzer 3 and ultrasonic generator 4, and pH tester 11 that is used to measure the pH value (hydrogen ion index) in the aqueous solution of potassium oxalate filled in the electrolytic cell 2.

The electrolytic cell 2 has a main body 2a filled with oxalic acid solution and an open-closed cover 2b that can cover the upper opening of said main body 2a of electrolytic cell. The main body 2a of electrolytic cell is made of a transparent material (e.g., transparent glass), so that the electrolysis in the electrolytic cell can be observed.

The electrolytic device 3 comprises a power supply unit 5 and a pair of electrodes 7a and 7b electrically connected to the power supply unit with wires 6, 6.

The power supply unit 5 is a device that applies predetermined current for predetermined time; or applies a predetermined voltage to flow determined current for predetermined time. While a predetermined voltage is applied to electrode 7a and 7b by the power supply unit 5, a predetermined constant current (e.g., 5A) flows through the electrodes, so that the aqueous solution of potassium oxalate in the electrolytic cell 2 is electrolyzed, and thereby carbonic acid gas and oxygen are produced from the positive electrode 7a; the amount of carbonic acid gas produced is defined as S(mol):

$$S = I \times t \times (1/9.65 \times 10^4) \times 1/n \qquad (1)$$

Wherein, I is in Ampere, t is in seconds, and n is the valence number of oxalic acid (n=2).

Said electrode 7a and 7b are both made of platinum; wherein, electrode 7a (anode) is made in coil form, while electrode 7b (cathode) is made in bar form. In addition, electrode 7a and 7b are inserted into the oxalic acid solution in the main body 2a of electrolytic cell through two holes on said cover 2b.

Said ultrasonic generator 4 has a main body 4a and an ultrasonic wave oscillator 4b electrically connected to said main body 4a. Said ultrasonic oscillator 4b is in pin form, with its base end (upper end) supported by supporting part 4c. Said supporting part 4c is mounted on the mounting part 8a on upper end of supporting base 8, and is almost perpendicular to said ultrasonic oscillator 4b.

The front end (lower end) of said ultrasonic oscillator 4b is inserted into the oxalic acid solution in the main body 2a of electrolytic cell through said cover 2b. When the ultrasonic oscillator 4b is inserted, it is almost coaxial to the center axis of the coil at inner side of the coil electrode 7a. In addition, the lower end of said ultrasonic oscillator 4b is located at one side of the upper end of electrode 7a, so that the ultrasonic wave applied from the front end of ultrasonic oscillator 4b acts to the entire electrode 7a.

Above ultrasonic generator 4 can reduce particle size of the carbonic acid gas produced from the positive electrode 7a; however, above ultrasonic generator 4 may not be required in the present invention.

Said operation controller 10 (12) is designed to control said electrolytic device 3 and said ultrasonic generator 4, and, in the embodiment, it mainly comprises: a receiving unit 15, designed to receive signals from said pH tester 11; storing unit, designed to store the magnitude of ultrasonic wave, current, and operating time that can form carbonic acid gas bubbles produced by electrolysis into the most suitable particle size (nanometer level) in a database; operation panel 17; displaying unit 18, and controlling unit 19 that controls said receiving unit 15, storing unit 16, operation panel 17, and displaying unit 18.

Said receiving unit 15 is designed to receive signals from the pH tester 11 and send the signals to the controlling unit 19; therefore, it can certainly receive signals for other parameters (e.g., temperature), depending on the function of said pH tester 11. Said storing unit 16 is designed to store the data required for the operation of said apparatus 1 for producing carbonic acid gas solution in advance; therefore, the data stored in said storing unit 16 can be read with the operation panel 17 to control said apparatus 1 for producing the carbonic acid gas solution.

In the examples, said operation controller 10 (12) also serves as a particle size controlling unit that controls the micro carbonic acid gas bubbles to a certain particle size range; said storing unit 16 stores the data for controlling the particle size of micro carbonic acid gas bubbles to nanometer level.

The particle size of micro carbonic acid gas bubbles can be controlled by intensity and duration of ultrasonic wave from the ultrasonic generator 4.

Said operation panel 17 is a key-input or touch-input unit; said display unit 18 can be a LCD (liquid crystal display).

Said controlling unit 19 is electrically connected to the receiving unit 15, storing unit 16, operation panel 17, and displaying unit 18, to control those units; in addition, it also controls operation of said electrolytic device 3 and the ultrasonic generator 4.

In addition, said pH tester 11 is designed to measure the pH value (hydrogen ion index) of carbonic acid gas solution in the step of mixing oxalic acid into the electrolyzed aqueous solution of potassium oxalate in the electrolytic cell 2; in this embodiment, the pH value signals from said pH tester is sent to the operation controller 10 (12), and may be displayed on the displaying unit 18 of the operation controller 10 (12).

In this embodiment, the pH tester 11 is used as the device to measure pH value, and here the function of said pH tester 11 is described. However, in the present invention, it can be used to measure not only the pH value but also the oxidation-reduction potential (ORP).

When said apparatus 1 for producing the carbonic acid gas solution is used to produce carbonic acid gas solution, an aqueous solution of potassium oxalate is filled into the main body 2a of said electrolytic cell, and then electrolyzed.

The concentration of the aqueous solution of potassium oxalate can be 0.1 M (mol/L) to 2 M; however, the concentration of the aqueous solution can be set as required according to the concentration of carbonic acid gas to be dissolved.

If the aqueous solution of potassium oxalate at 0.1 M (mol/L) is electrolyzed, carbonic acid gas bubble attached to skin stably can be obtained; however, if the concentration of the aqueous solution of potassium oxalate is lower than 0.1 M (mol/L), the unique effect of carbonated spring (i.e., numerous water bubbles on skin surface and ruddy skin) will not be obtained, even if oxalic acid is added in the subsequent procedure to produce a great deal of carbonic acid gas instantaneously; in addition, if the concentration of the aqueous solution of potassium oxalate is higher than 2 M, the potassium oxalate can not be dissolved completely at room temperature; therefore, the optimal maximum concentration of potassium oxalate is 2 M.

The current flowing from the power supply unit 5 of electrolytic device 3 to the electrodes 7a and 7b as well as the operation duration are predetermined by the operation controller 10.

The current and duration are determined in accordance with the amount and concentration of potassium oxalate and the sizes of the electrodes. In the experiment of the present invention, if the amount and concentration of potassium oxalate to be electrolyzed are high, the current should be high (e.g., about 5 A), and the duration should be long.

Furthermore, in order to control the particle size of micro carbonic acid gas bubbles produced by electrolyzing potassium oxalate within the specified range, the ultrasonic wave intensity of the ultrasonic generator 4 is set.

In the apparatus for producing carbonic acid gas solution in above structure, with the operation controller 10, the voltage to be applied to the electrodes 7a and 7b and the duration of voltage application are predetermined; when the aqueous solution of potassium oxalate is electrolyzed, carbonic acid gas and oxygen are produced from the positive electrode 7a, and said carbonic acid gas and oxygen are partially dissolved in the aqueous solution of potassium oxalate.

Furthermore, as the solution is electrolyzed, the ultrasonic generator 4 is started up to produce ultrasonic wave with the ultrasonic oscillator 4b. At that time, said ultrasonic wave acts directly to the carbonic acid gas bubbles produced from electrode 7a, so that the bubbles rupture and form micro bubbles, which are dissolved in the aqueous solution of potassium oxalate.

In addition, hydrogen is produced from the negative electrode 7b and is partially dissolved in the aqueous solution of potassium oxalate.

Now, the first aqueous solution filled in the electrolytic cell 2 enters into a state short of electrons (oxidation field) under electrolysis.

As the result, carbonic acid gas solution in oxidation field state with hydrogen, oxygen, and micro carbonic acid gas bubbles dissolved in it, can be produced. Said micro bubbles are referred to as nanometer bubbles (bubble), which are invisible.

If the carbonic acid gas bubbles produced from the electrode are small enough, it is unnecessary to use said ultrasonic generator 4.

In addition, since the aqueous solution of potassium oxalate is ionized into oxalic acid radical ion and potassium ion in advance, the energy of electrolysis is used in the quick production of carbonic acid gas rather than ionization in the initial stage. Therefore, with potassium oxalate, carbonic acid gas can be produced in a shorter time.

In that way, carbonic acid gas solution (aqueous solution of potassium oxalate) with a great deal of micro bubbles dissolved can be obtained; however, the unique effect of carbonated spring (i.e., numerous water bubbles and ruddy skin) can not be obtained sufficiently merely by electrolyzing the aqueous solution of potassium oxalate. Therefore, in the present invention (this embodiment), in order to obtain a great deal of carbonic acid gas, aqueous solution of oxalic acid, which is used as the second aqueous solution, is added into the electrolyzed raw aqueous solution, i.e., the first aqueous solution (aqueous solution of potassium oxalate).

In that way, carbonic acid gas bubbles will be produced with the following chemical scheme:

$$(COOH)_2 + O_2 + H_2 \rightarrow 2CO_2 + 2H_2O \tag{1}$$

Above electrochemical reaction $C_2O_4^{2-} \rightarrow 2CO_2 + 2e^-$ at the anode produces electrons; therefore, the electrons reacts with water (i.e., electrolysis of water); at the cathode, hydrogen is produced through the following electrochemical reaction; said hydrogen is used in above scheme (1).

$$2H_2O + 2e^- \rightarrow H_2 + 2OH^- \tag{2}$$

If the raw aqueous solution is alkaline, the hydroxide radical ion (OH–) in above scheme (2) will produce oxygen through the following electrochemical reaction at the anode; said oxygen is used in above scheme (1).

$$4OH^- \rightarrow 2H_2O + O_2 + 4e^-$$

Above reaction mechanism is supposed as follows.

That is to say, the following reaction occurs in the first aqueous solution:

$$HCO_3^- \rightarrow CO_2 + OH^-$$

or $$(COO^-)_2 \rightarrow 2CO_2 + O_2 + 2e^-$$

With above scheme, nanometer $CO_2$ particles are produced; then, the $CO_2$ produced during decomposition of carboxylic acid (e.g., oxalic acid) grows on the existing $CO_2$ nanometer particles (nuclei) into $CO_2$ bubbles.

With above scheme, the oxalic acid added later and the oxalic acid in the aqueous solution of oxalic acid in oxidation field state resulted from electrolysis react, so that a great deal of micro carbonic acid gas bubbles are produced instantaneously.

In the carbonated water produced in that way, the oxygen and hydrogen produced in electrolysis react with the oxalic acid in the aqueous solution of oxalic acid to produce micro carbonic acid gas bubbles, and the carbonic acid gas bubbles are dissolved in the aqueous solution. When hands dip into the aqueous solution of oxalic acid with micro carbonic acid gas bubbles dissolved, the unique effect (i.e., numerous water bubbles on skin surface and ruddy skin) is obtained.

In this embodiment, when producing the carbonic acid gas solution with micro carbonic acid gas bubbles dissolved, the apparatus does not need gas dissipation device, carbonic acid gas bomb, gas separator, or compressor that are required in the method for producing carbonated spring in the prior art. Therefore, the apparatus can easily produce carbonic acid gas solution with micro carbonic acid gas bubbles dissolved at a low cost.

In addition, since the oxalic acid ion in the aqueous solution is ionized in advance, carbonic acid gas solution can be produced in a shorter time.

In addition, in this embodiment, as the aqueous solution of potassium oxalate in electrolytic cell 2 is electrolyzed with the electrolytic device 3 to produce carbonic acid gas, ultrasonic wave is applied on the carbonic acid gas bubbles with the ultrasonic generator 4, to form micro bubbles from above bubbles; then, said micro bubbles are dissolved in the aqueous solution of potassium oxalate; therefore, the concentration of the carbonic acid gas solution with micro bubbles dissolved can be increased effectively.

In above case, since the ultrasonic oscillator 4b of said ultrasonic generator 4 is inserted at the inner side of coil electrode 7a of said electrolytic device 3, the ultrasonic wave can be effectively and uniformly applied to the bubbles of carbonic acid gas produced from electrode 7a to form micro bubbles. As the result, carbonic acid gas solution with micro bubbles dissolved can be produced effectively as the aqueous solution of potassium oxalate is electrolyzed.

Other embodiments of the apparatus for producing the carbonic acid gas solution in the present invention will be described, with reference to FIG. 2 to FIG. 4.

The apparatuses for producing carbonic acid gas solution shown in those drawings differ from the apparatus for producing carbonic acid gas solution shown in FIG. 1 in the form and configuration of electrodes as well as the configuration of ultrasonic oscillator. Hereunder the differences are described in detail; the identical parts are denoted with identical reference sign, and thereby the description of them is omitted or simplified.

The apparatus for producing carbonic acid gas solution 21 comprises: an electrolytic cell 2, with a main body 2a on a supporting base 22 and an open-closed cover 2b that can cover the upper opening of said main body 2a of electrolytic cell; electrolytic device 3; ultrasonic generator 4; operation controller 10 (12), designed to control said electrolytic device 3 and said ultrasonic generator 4; pH tester 11, designed to measure the pH value (hydrogen ion index) of the first aqueous solution (i.e., oxalic acid solution) filled in said electrolytic cell 2.

In above apparatus for producing carbonic acid gas solution 21, in the electrolytic cell 2 with electrodes 7a and 7b, the first aqueous solution is electrolyzed by applying DC voltage between the electrodes 7a and 7b in the electrolytic cell 2, to form an oxidation field short of electrons in said aqueous solution; then, the second aqueous solution with carboxylic acid dissolved is mixed into the first aqueous solution in oxidation field state, so that the first aqueous solution in oxidation field state obtains electrons to be reduced, and the carboxylic acid is oxidized, to produce carbonic acid gas in the mixed aqueous solution.

In addition, in these embodiments, the pH tester 11 can also be switched to measure the oxidation-reduction potential (ORP).

Said electrolytic device 3 comprises a power supply unit 5, and 4 electrodes 25a, 25b, 26a and 26b electrically connected to the power supply unit 5 with wires 6, 6. Said electrodes 25a and 26a are anode, while said electrodes 25b and 26b are cathode. Said electrodes 25a and 25b constitute an electrode group 25, while said electrodes 26a and 26b constitute an electrode group 26. That is to say, the embodiment has two electrode groups 25 and 26.

Said electrodes 25a, 25b, 26a and 26b are rectangular plates almost in the same shape; furthermore, said electrodes 25a, 25b, 26a and 26b are made of platinum or manufactured by coating platinum on titanium plates, titanium alloy plates, or appropriate metal plates.

The upper end of each electrode 25a, 25b, 26a and 26b is connected to one end of a L-shaped conductor 28 respectively; and the other end of said conductor 28 protrudes upwards above the electrolytic cell 2. The upper portion of the other end of said conductor 28 is connected with said wires 6, 6.

In addition, said electrode 25a and electrode 25b are parallel to each other at a specified spacing; similarly, said electrode 26a and electrode 25b are parallel to each other at a specified spacing.

As shown in the drawing, said electrodes 25 and 26 can be arranged vertically or horizontally. If said electrodes 25 and 26 are arranged horizontally, appropriate holes are formed on said electrodes, so that the bubbles produced from said electrodes can pass upwards through said holes.

In addition, the electrode group 25 composed of electrodes 25a and 25b, and the electrodes 26 composed of electrodes 26a and 26b are separated from each other in left-to-right direction, and said ultrasonic oscillator 4b is mounted between them.

The supporting part of said ultrasonic oscillator 4b is supported on the support 22a on the supporting base 22 by means of an arm 22b. Said arm 22b can move in vertical direction along the support 22a and rotate in horizontal direction, and can be fixed to said support 22a at a specified position in vertical direction and can't rotate in horizontal direction. In that way, the position of said ultrasonic oscillator 4b can be adjusted vertically and horizontally.

When carbonic acid gas solution is produced with said apparatus for producing carbonic acid gas solution 21, the first aqueous solution is filled into the electrolytic cell 2. Here, an aqueous solution with carboxylic acid dissolved is used as the first aqueous solution. Examples of the carboxylic acid can be oxalic acid, acetic acid, citric acid, succinic acid, malonic acid, fumaric acid, lactic acid, malic acid, tartaric acid, etc.

Here, the first aqueous solution is preferably a buffer solution composed of a combination of carboxylic acid and monovalent cation thereof. Examples of said monovalent cation can be Li, Na, K, Ru, Ce, Fr, etc.

Specifically, examples of the combination of carboxylic acid and monovalent cation thereof include the combination of oxalic acid and potassium oxalate, acetic acid and sodium acetate, citric acid and sodium citrate, succinic acid and sodium succinate, malonic acid and sodium malonate, fumaric acid and sodium fumarate, lactic acid and sodium lactate, malic acid and sodium malate, tartaric acid and sodium tartrate, etc.

The first aqueous solution can also be an aqueous solution comprising any one of acidic fruit juice or extract of tea as the major component. Specifically, examples of the acidic fruit juice can be citrus, shaddock, orange (Valencia orange), grapefruit, lemon, sour orange, apple, grape, peach, apricot, cherry, strawberry, pineapple, passion fruit, banana, Japanese apricot, melon, etc.

In addition, if the first aqueous solution is an aqueous solution comprising any one of acidic fruit juice or extract of tea as the major component, preferably carbonate is added into the first aqueous solution, in order to facilitate decomposition of carboxylic acid in the acidic fruit juice or the extract of tea and improve efficiency of electrolysis. After carbonate is added into the first aqueous solution, the carbonate is decomposed, and thereby the pH value in the first aqueous solution is increased, and the electrolytic electrolysis is accelerated; in addition, the carbonic acid gas produced in the carbonate reaction and the carbonic acid gas produced by mixing the second aqueous solution in the oxidation field coexist in the mixed solution; and as a result, the concentration of carbonic acid gas in the aqueous solution is increased effectively.

In addition, in this embodiment, said carbonate is preferably sodium bicarbonate. Sodium bicarbonate is soluble in water, and produces sodium ion that combines with carboxylic acid through the following reaction and thereby delivers cushioning effect; therefore, it will not increase the pH value.

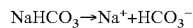

$$NaHCO_3 \rightarrow Na^+ + HCO_3^-$$

$$HCO_3^- + H^+ \rightarrow H_2CO_3 \rightarrow CO_2 + H_2O$$

The first aqueous solution is filled into electrolytic cell 2 and then is electrolyzed by applying DC voltage between electrodes 7a and 7b in electrolytic cell 2.

Above electrolysis is preferably carried out till the pH value in the first aqueous solution is ≧6.

That is because, if the pH value is ≧6, carbonic acid gas will be produced stably; however, if the pH value is <6, the carbonic acid gas will be dissolved in the ions, and the concentration of carbonic acid gas will not increase.

That is to say, the following reaction occurs at the anode:

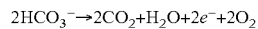

$$2HCO_3^- \rightarrow 2CO_2 + H_2O + 2e^- + 2O_2$$

If the pH value is ≧6, above carbonic acid gas will form micro bubbles in the electrolyzed solution; if the pH value is <6, the reverse reaction will occur, and the concentration of carbon dioxide will not increase.

Here, if a buffer solution is used in the first aqueous solution, the pH value in the first aqueous solution will not become alkaline, due to the cushioning effect of the buffer solution; therefore, the first aqueous solution can be electrolyzed stably.

In addition, when sodium bicarbonate is added in the electrolysis process, sodium bicarbonate will react with the acidic aqueous solution and produce carbonic acid gas, which will not affect electrolysis.

The dissolvability of the first aqueous solution with carboxylic acid dissolved depends on the raw materials. In the embodiment, if the concentration of the first aqueous solution is 0.1 M (mol/L)~1M, it is enough to form an oxidation field; however, in consideration of the final concentration of carbonic acid gas, it is better to set the concentration of the aqueous solution appropriately.

A 0.1M (mol/L) aqueous solution is enough to ensure carbonic acid gas bubbles to attach to skin stably; however, if the concentration is less than 0.1M (mol/L), the unique feature of carbonated spring (i.e., numerous bubbles on skin surface and ruddy skin) will not be obtained, even if oxalic acid is added in the subsequent procedure to produce a great deal of carbonic acid gas instantaneously.

However, when the fruit juice or the extract of tea is used at a concentration ≦0.1M (mol/L), carbonate can be utilized to produce carbonic acid gas and form the oxidation field, so as to increase the amount of carbonic acid gas dissolved in the first aqueous solution; then, when the second aqueous solution is added in the subsequent procedure, the carbonic acid gas dissolved in the first aqueous solution will serve as nuclei to produce a great deal of carbonic acid gas; as a result, enough concentration of carbonic acid gas (≧400 ppm) can be obtained, and thereby the unique feature of carbonated spring (i.e., numerous bubbles on skin surface and ruddy skin) can be obtained.

The current flowing from the power supply unit 5 of electrolytic device 3 to the electrodes 25a, 25b, 26a and 26b as well as the operation duration are predetermined with the operation controller 10.

Here, in order to control the particle size of micro carbonic acid gas bubbles produced by reaction between the first aqueous solution and the second aqueous solution within a certain range, the intensity of ultrasonic wave of the ultrasonic generator 4 can also be set.

As described above, when the first aqueous solution is electrolyzed in electrolytic cell 2, an oxidation field short of electrons can be formed in said aqueous solution.

When the second aqueous solution with carboxylic acid dissolved is mixed into the first aqueous solution in oxidation field state short of electrons, the first aqueous solution in oxidation field state will obtain electrons and will be deoxidized, and the carboxylic acid will be oxidized, so that carbonic acid gas is produced in the mixed aqueous solution.

Here, the carboxylic acid dissolved in the second aqueous solution is the same as that in the first aqueous solution, and its examples can be oxalic acid, acetic acid, citric acid, succinic acid, malonic acid, fumaric acid, lactic acid, malic acid, tartaric acid, etc.

In addition, the second aqueous solution can be an aqueous solution comprising any one of acidic fruit juice or extract of tea as the major component. Specifically, the acidic fruit juice can be citrus, shaddock, orange (Valencia orange), grapefruit, lemon, sour orange, apple, grape, peach, apricot, cherry, strawberry, pineapple, passion fruit, banana, Japanese apricot, or melon, etc.

In this embodiment, the first aqueous solution filled in the electrolytic cell forms a state short of electrons (oxidation field) under electrolysis. When the second aqueous solution with carboxylic acid dissolved is mixed into the first aqueous solution in oxidation field state short of electrons, electron donating reaction occurs in the first aqueous solution, so that the carboxylic acid is oxidized, and carbonic acid gas is produced in the mixed aqueous solution.

For example, as an example of carboxylic acid, the reaction of oxalic acid is as follows:

$$(COOH)_2 \rightarrow 2CO_2 + 2H^+ + 2e^-$$

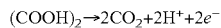

In the first aqueous solution where the oxidation field is formed under electrolysis, above electron donating reaction facilities the reaction of formation of carbonic acid gas.

In addition, by adjusting the amount of the second aqueous solution added into the first aqueous solution in oxidation field state, the pH value in the mixed aqueous solution can be controlled in a range of 5-7.

With the method for producing carbonic acid gas solution in above embodiment, after the first aqueous solution is electrolyzed to a pH value $\geqq 6$ and produces carbonic acid gas stably, micro carbonic acid gas bubbles exist in the electrolyzed first aqueous solution; then, the second aqueous solution is added into the first aqueous solution in oxidation field state, in such an amount that the pH value in the mixed solution is in a range of 5-7; as a result, micro carbonic acid gas bubbles and carbonic acid gas produced instantaneously by oxidizing carboxylic acid in the first aqueous solution coexist in the mixed solution; therefore, the concentration of carbonic acid gas in the mixed solution is increased effectively.

In addition, after the second aqueous solution is added, the mixed solution has a pH value in a range of 5-7 (i.e., in the weakly acidic area); therefore, that solution has mild effect to skin.

In above embodiment, the second aqueous solution is added, till the pH value in the mixed aqueous solution reaches to 5-7. However, the present invention is not limited to those embodiments; for example, an acidic solution can be added after the first aqueous solution is electrolyzed to a pH value $\geqq 6$ and before the second aqueous solution is added, so that the pH value of the first aqueous solution is adjusted to 5-7 range; then, the second aqueous solution can be added, and the pH value is kept within the range of 5-7.

With above method, before the second aqueous solution is added, the pH value in the first aqueous solution is adjusted to 5-7; therefore, it does not need to utilize the second aqueous solution to keep the pH value within the range of 5-7; therefore, the formation of carbonic acid gas can also be accelerated within pH range of 5-7 even the concentration of the second aqueous solution is lowered (not strongly acidic).

With above embodiment, the present invention facilitates the formation of carbonic acid gas, and the carbonic acid gas is dissolved in aqueous solution; therefore, the present invention does not need gas dissipation device, carbonic acid gas bomb, gas separator, and compressor that are required in the methods for producing carbonated spring in the prior art.

Therefore, the present invention can produce carbonic acid gas solution at a low cost easily.

In the apparatus for producing carbonic acid gas solution 21 in above embodiment, the electrodes are in plate form, and multiple electrode groups 25 and 26 composed of electrodes 25a, 25b, 26a and 26b are provided, so as to produce a great deal of carbonic acid gas, oxygen, and hydrogen.

In addition, the ultrasonic oscillator 4b is provided between the electrode groups 25 and 26, so that the ultrasonic wave acts effective and uniformly to the bubbles produced from said electrode 25a and 26a, in order to form micro bubbles. As a result, carbonic acid gas solution with a large amount of micro bubbles (raw solution) can be produced effectively.

In above embodiment, the electrolysis of the first aqueous solution is carried out with reference to pH value; however, the present invention is not limited to that embodiment; for example, the electrolysis can also be carried out with reference to oxidation-reduction potential. In that case, the reference oxidation-reduction potential is the most stable oxidation-reduction potential (the actual oxidation-reduction potential will not rise above it); the oxidation-reduction potential depends on the raw materials of the aqueous solution, that is to say, the first aqueous solution is electrolyzed, till the oxidation-reduction potential becomes a negative MV value not higher than said reference oxidation-reduction potential.

Then, the second aqueous solution is added.

Even if the electrolysis is carried out with reference to oxidation-reduction potential, the first aqueous solution is still electrolyzed to form a state short of electrons (oxidation field); then, the second aqueous solution is mixed into the first aqueous solution in oxidation field state, so that an electron donating reaction occurs in the mixed aqueous solution and the carboxylic acid is oxidized, and thereby a great deal of carbonic acid gas is produced instantaneously in the first aqueous solution.

Figure 2:
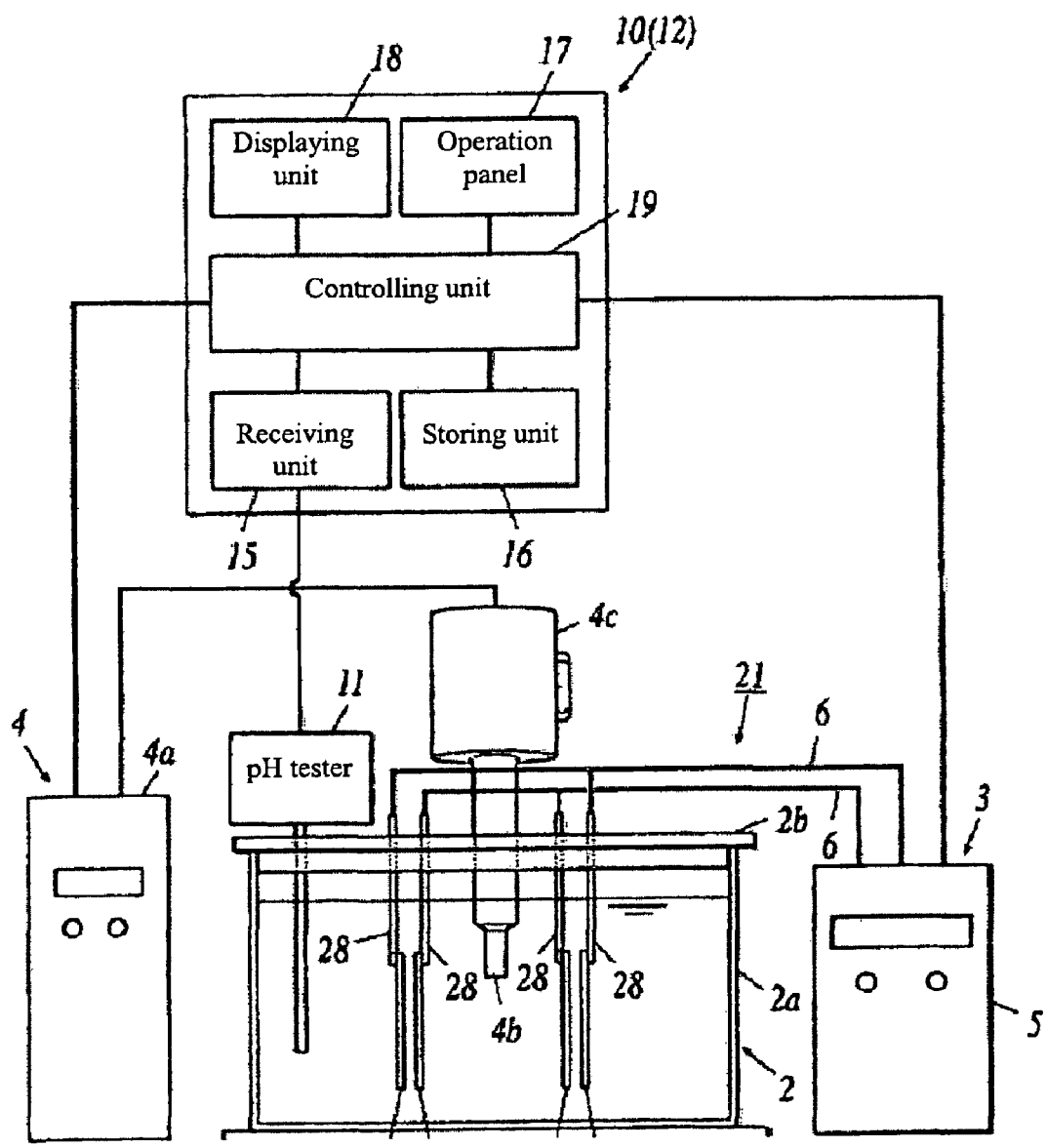
FIG. 2 is a schematic front view of the structure of apparatus for producing carbonic acid gas solution in another embodiment of the invention.
Figure 3:
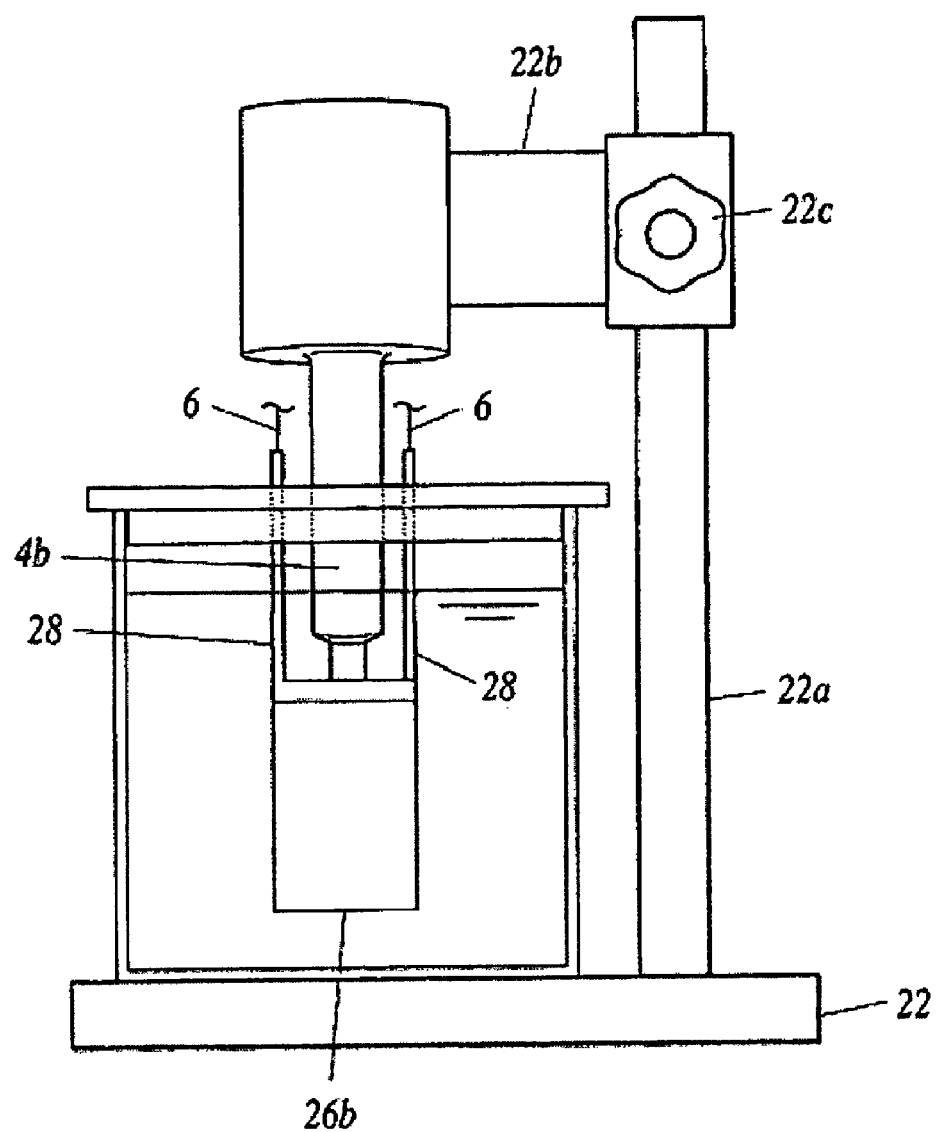
FIG. 3 is a schematic side view of the structure of apparatus for producing carbonic acid gas solution in another embodiment of the invention.
Figure 4:
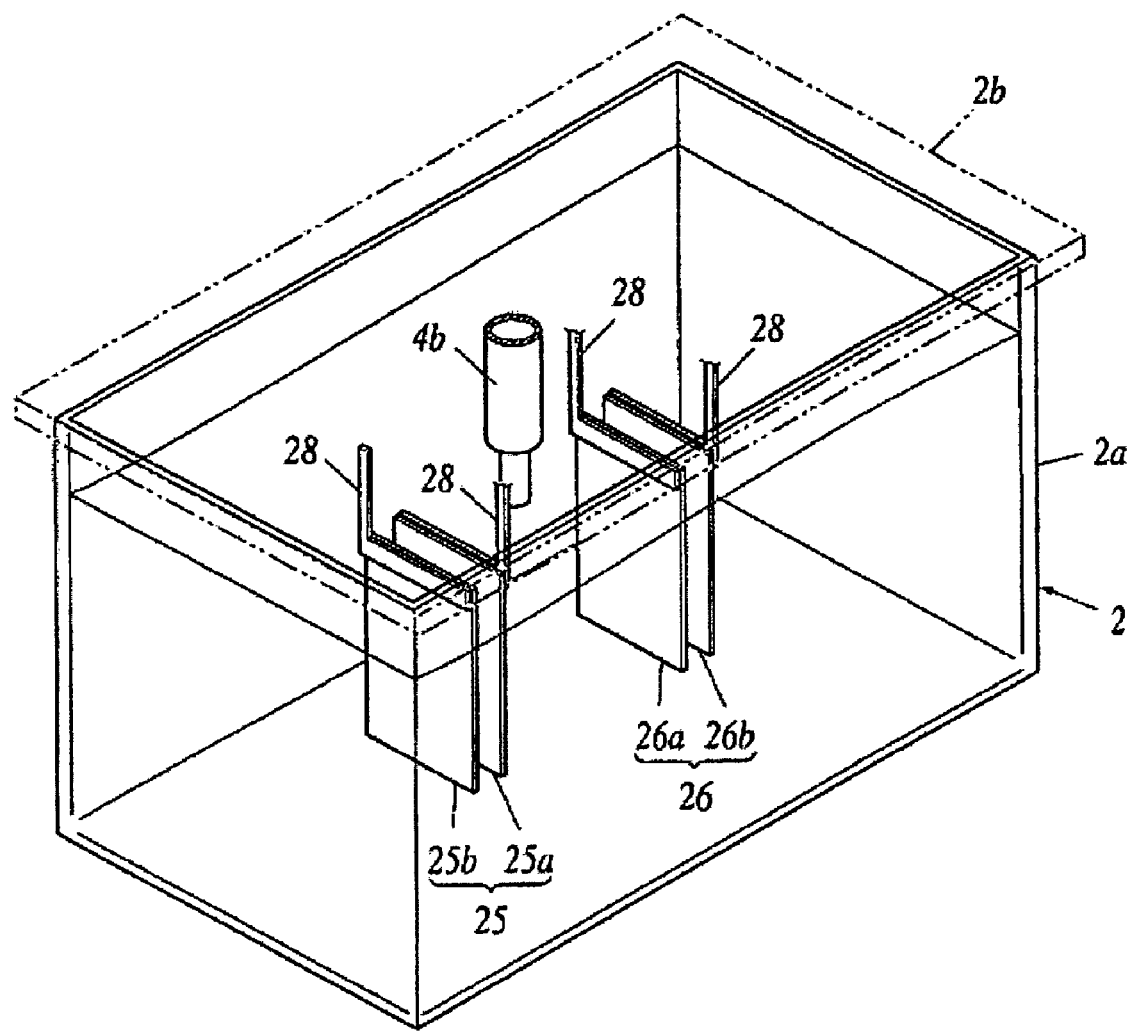
FIG. 4 is a perspective view of the electrode group provided in the electrolytic tank in the apparatus for producing carbonic acid gas solution in another embodiment of the invention.

With potassium oxalate as the first aqueous solution, the method for producing carbonic acid gas solution by using the apparatus for producing carbonic acid gas solution 21 shown in FIG. 2 to FIG. 4 is as follows.

First, the aqueous solution of potassium oxalate is filled in the main body 2a of electrolytic cell, and then is electrolyzed.

The concentration of the aqueous solution of potassium oxalate can be 0.1 M (mol/L) ~2 M; however, the concentration of the aqueous solution can be set as required depending on the concentration of carbonic acid gas to be dissolved.

A 0.1M (mol/L) aqueous solution is enough to ensure carbonic acid gas bubbles to attach to skin stably; however, if the concentration is less than 0.1 M (mol/L), the unique feature of carbonated spring (i.e., numerous bubbles on skin surface and ruddy skin) will not be obtained, even if oxalic acid is added in the subsequent procedure to produce a great deal of carbonic acid gas instantaneously.

However, if the concentration of the aqueous solution of potassium oxalate is ≧2M, the potassium oxalate can not be dissolved completely at room temperature; therefore, the maximum concentration is preferably up to 2M.

With the operator controller 10, the current from the power supply unit 5 of the electrolytic device 3 to the electrodes 25a, 25b, 26a, and 26b and the duration are predetermined; and at the same time, in order to control the particle size of micro carbonic acid gas bubbles produced in electrolysis of potassium oxalate within the specified range, the intensity of ultrasonic wave of the ultrasonic generator 4 is set.

With the operation controller 10, the aqueous solution of potassium oxalate is electrolyzed by applying predetermined voltage on electrodes 25a, 25b, 26a, and 26b, to produce carbonic acid gas and oxygen from the positive electrode 25a and 26a; in addition, the carbonic acid gas and oxygen are partially dissolved in the aqueous solution of potassium oxalate.

Furthermore, as the solution is electrolyzed, the ultrasonic generator 4 is started up to produce ultrasonic wave with the ultrasonic oscillator 4b. At that time, said ultrasonic wave acts directly to the carbonic acid gas bubbles produced from electrode 25a and 26a, so that the bubbles rupture and form micro bubbles, which are dissolved in the aqueous solution of potassium oxalate.

Hydrogen is produced from the negative electrode 25b and 26b, and is partially dissolved in the aqueous solution of potassium oxalate.

As a result, carbonic acid gas solution with hydrogen, oxygen, and micro carbonic acid gas bubbles dissolved can be produced. Said micro bubbles are referred to as nanometer bubbles (bubble), which are invisible.

If the carbonic acid gas bubbles produced from the electrode are small enough, it is unnecessary to use said ultrasonic generator 4.

In addition, since the aqueous solution of potassium oxalate is ionized into oxalic acid radical ion and potassium ion in advance, the energy of electrolysis is used in the quick production of carbonic acid gas rather than ionization in the initial stage. Therefore, with potassium oxalate, carbonic acid gas can be produced in a shorter time.

In the apparatus for producing carbonic acid gas solution 21 in above embodiment, the electrodes are in plate form, and multiple electrode group 25 and 26 composed of electrodes 25a, 25b, 26a and 26b are provided, so as to produce a great deal of carbonic acid gas, oxygen, and hydrogen.

In addition, the ultrasonic oscillator 4b is provided between the electrode groups 25 and 26, so that the ultrasonic wave acts effectively and uniformly to the bubbles produced from said electrodes 25a and 26a, in order to form micro bubbles. As a result, carbonic acid gas solution with a large amount of micro bubbles (raw solution) can be produced effectively.

In addition, since the aqueous solution of potassium oxalate is ionized into oxalic acid radical ion and potassium ion in advance, the energy of electrolysis is used in the quick production of carbonic acid gas rather than ionization in the initial stage. Therefore, with potassium oxalate, carbonic acid gas can be produced in a shorter time.

In this embodiment, when the aqueous solution of oxalic acid is added into said electrolyzed aqueous solution of potassium oxalate, the oxalic acid reacts with the oxygen produced at anode and the hydrogen produced at cathode, so that a great deal of micro carbonic acid gas bubbles are produced instantaneously.

A great deal of micro carbonic acid gas bubbles are produced instantaneously through above chemical reaction of oxalic acid, and micro carbonic acid gas bubbles are produced in electrolysis of above aqueous solution of potassium oxalate; therefore, a great deal of micro carbonic acid gas bubbles are dissolved in the aqueous solution.

Hereunder another embodiment of the apparatus for producing carbonic acid gas solution in the present invention will be described, with reference to FIG. 5.

The apparatuses for producing carbonic acid gas solution shown in those drawings differ from the apparatus for producing carbonic acid gas solution shown in FIG. 1 in the form and configuration of electrodes as well as the configuration of ultrasonic oscillator. Hereunder the differences are described in detail; the identical parts are denoted with identical reference sign, and thereby the description of them is omitted or simplified.

The carbonic acid gas solution producing apparatus 40 mainly comprises: an electrolytic cell 2A designed to electrolyze the first aqueous solution; electrodes 7a,7b in the electrolytic cell; an electrolytic device 3A, which applies a DC voltage on the electrodes 7a,7b to electrolyze the first aqueous solution in the electrolytic cell 2A; a filling container 50, which is filled with the second aqueous solution with carboxylic acid dissolved in it; a tester 11, which measures any one or the combination of pH value and oxidation-reduction potential of the electrolyzed aqueous solution in the electrolytic cell 2A; a controller 3A, which adds the aqueous solution with carboxylic acid dissolved in said filling container 50 into said electrolytic cell 2A when the pH value measured by the tester 11 is ≧7 or the oxidation-reduction potential measured by the tester 11 is a negative MV value; a reaction vessel 51, in which the first aqueous solution electrolyzed in the electrolytic cell 2A reacts with the second aqueous solution; and a circulating pump 52, which is located between the electrolytic cell 2A and the reaction vessel 51, and circulates the aqueous solution between the electrolytic cell and the reaction vessel.

In this embodiment, said electrolytic cell 2A is connected to said reaction vessel 51 through pipes 57 and 58; circulating pump 52, flow meter 53, and regulating valve 54, which are designed to regulate the flow through said circulating pump, are mounted on pipe 57.

The outlet of filling container 50 is connected to electrolytic cell 2A; a regulating valve 55 is mounted on th2 pipe 59 between said outlet and said electrolytic cell 2A, to regulate the volume of the second aqueous solution from the filling container 50.

An outlet pipe 60 designed to discharge aqueous solution is mounted on reaction vessel 51; a valve 56 is mounted on said pipe 60.

Above electrolytic cell 2A is in an enclosed structure; the aqueous solution from circulating pump 52 flows through the suction inlet below said electrolytic cell 2A into electrolytic cell 2A, and then flows by electrodes 7A and 7b, and flows through the outlet on electrolytic cell 2A and pipe 58 into the inlet below the reaction vessel 51.

Above reaction vessel 51 is preferably a bath vessel. If said reaction vessel 51 is a bath vessel, a home bathroom can be turned into a carbonated spring bathroom easily. In this embodiment, the electrolytic device and the controlling unit are controlled by the same controller; said controller adds the aqueous solution with carboxylic acid dissolved in the filling container 50 into the electrolytic cell 2A. Above controller 3A is connected with signal wire 3B to regulate the flow through the circulating pump; in addition, the regulating valve 54 is connected to the signal wire 3C, and the flow meter 53 is connected to the signal wire 3D; therefore, the circulating water flow is controlled with a computer.

Furthermore, in this embodiment, pH tester 11 is connected to signal wire 3E; the regulating valve 55 designed to regulate the flow from filling container 50 is connected to the signal wire 3F; after the pH value or oxidation-reduction potential signal is received, the flow of the second aqueous solution to the pipe 58 can be regulated with the regulating valve 55.

When the apparatus for producing carbonic acid gas solution 40 in above structure is used to produce carbonic acid gas solution, the first aqueous solution is added in the pipeline with electrolytic cell 2A and reaction vessel 51.

In addition, the second aqueous solution is filled in the filling container 50.

The two aqueous solutions can be any of the above-mentioned aqueous solution.

For example, after the first aqueous solution comprising any one of acidic fruit juice or extract of tea as the major component and sodium bicarbonate are added, the circulating pump 52 is started, to circulate the first aqueous solution filled in the pipeline.

With the electrolytic device 3A, the first aqueous solution (the aqueous solution comprising any one of acidic fruit juice or extract of tea as the major component) is electrolyzed by applying DC voltage between electrodes 7a and 7b in electrolytic cell 2A, so that the carboxylic acid in the aqueous solution is electrolyzed, till the pH value in the first aqueous solution in electrolytic cell 2A is $\geqq 6$, and the first aqueous solution in electrolytic cell 2A forms an oxidation field short of electrons.

In this embodiment, sodium bicarbonate reacts with the acid and produces carbonic acid gas; the sodium ion produced through the following reaction combines with carboxylic acid in the fruit juice and delivers cushioning effect; therefore, the pH value will not rise.

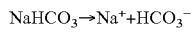
$$NaHCO_3 \rightarrow Na^+ + HCO_3^-$$

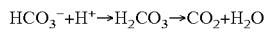
$$HCO_3^- + H^+ \rightarrow H_2CO_3 \rightarrow CO_2 + H_2O$$

Through above operations, the second aqueous solution with carboxylic acid dissolved is mixed into the first aqueous solution in oxidation field state, so that the pH value will not drop into the weakly acidic area; the first aqueous solution in oxidation field state obtains electrons and is deoxidized, and the carboxylic acid in the second aqueous solution is oxidized; as a result, carbonic acid gas is produced in the mixed solution.

If the second aqueous solution is strongly acidic citric acid or acetic acid, the pH value of the first aqueous solution can be controlled within weakly acidic range easily.

Those operations are controlled with the program preset in the controller 3A; virtually, the first aqueous solution and the second aqueous solution are filled under the control of said controller 3A.

Furthermore, the method for producing carbonic acid gas solution with the apparatus shown in FIG. 5 can also be as follows.

That is to say, in the electrolytic cell 2A with electrodes, the first aqueous solution is electrolyzed by applying DC voltage between electrode 7a and 7b, to increase the pH value in the first aqueous solution to about 7; whenever the pH value reaches to about 7, the second aqueous solution is supplied from the filling container 50 to reduce the pH value in the first aqueous solution.

With above operation, the pH value in the first aqueous solution will not move into alkaline range, but is kept in the weakly acidic area (6-7), so that an oxidation field short of electrons is formed in the first aqueous solution; then, the second aqueous solution with carboxylic acid dissolved is mixed into the first aqueous solution in oxidation field state, so that the first aqueous solution in oxidation field obtains electrons and is deoxidized, and the carboxylic acid in the second aqueous solution is oxidized; as a result, carbonic acid gas is produced in the mixed aqueous solution.

In above method, whenever the pH value reaches to about 7, an acidic solution that can decrease the pH value is added into the first aqueous solution, so that the pH value in the first aqueous solution will not move to the alkaline range but is kept in the faintly acid area (6-7), to form an oxidation field short of electrons in the first aqueous solution, which supports stable production of carbonic acid gas for a long time; when the second aqueous solution with carboxylic acid dissolved is mixed into the first aqueous solution in oxidation field state, the first aqueous solution in oxidation field state obtains a great deal electrons and thereby is deoxidized, and the carboxylic acid in the second aqueous solution is oxidized, and thereby further facilitates production of carbonic acid gas in the mixed aqueous solution.

The first aqueous solution and the second aqueous solution used in above operations can be an appropriate combination of the above-mentioned aqueous solutions.

In this embodiment, the first aqueous solution comprising any one of acidic fruit juice or extract of tea as the major component reacts with sodium bicarbonate to produce carbonic acid gas; in addition, the electrolysis is accelerated by increasing the pH value in the first aqueous solution; the carbonic acid gas produced from carbonate reaction and the carbonic acid gas produced by mixing the second aqueous solution in the oxidation field coexist; as a result, the concentration of carbonic acid gas in the mixed aqueous solution is increased.

Especially, in this embodiment, the circulating pump 52 makes the first aqueous solution in electrolytic cell 2A circulate between reaction vessel 51 and electrolytic cell 2A; therefore, specific volume of aqueous solution flows into electrolytic cell 2A continuously, so that a great deal of aqueous solution is effectively electrolyzed; therefore, the efficiency of electrolysis of the aqueous solution is improved; in addition, the circulating aqueous solution is stored in reaction vessel 51 temporarily; when the second aqueous solution flows out from filling container 50, the first aqueous solution and the second aqueous solution react in said reaction vessel 51 and thereby produce a great deal of carbonic acid gas instantaneously in said reaction vessel 51.

The apparatus does not need the gas dissociation device, carbonic acid gas bomb, gas separator, or compressor, etc., which are required in the method for producing carbonated spring in the prior art.

Therefore, the apparatus can easily produce carbonic acid gas solution with micro carbonic acid gas bubbles dissolved at a low cost.

In this embodiment, the aqueous solution filled in the electrolytic cell 2A is electrolyzed with the electrolytic device 3A, and the pH value or oxidation-reduction potential is measured with the tester 11; therefore, the aqueous solution can be controlled in the appropriate oxidation field state.

Carbonated spring can be produced easily by controlling the addition of aqueous solution of carboxylic acid in the filling container 50 into the electrolytic cell 2A with the controller 3A.

In addition, if the reaction vessel 51 is a bath vessel, carbonated spring can be produced easily in home.

In the carbonic acid gas solution produced through above operations, a great deal of micro (nanometer level) carbonic acid gas bubbles are produced through the following reaction mechanism; therefore, the carbonic acid gas solution delivers the unique effect of carbonated spring (i.e., numerous water bubbles on skin surface and ruddy skin), and can facilitate increase and dilatation of capillary bed and improve blood circulation in skin.

That is to say, when the first aqueous solution with carboxylic acid dissolved is electrolyzed, hydrogen, oxygen, and carbonic acid gas are produced.

The reaction scheme is as follows:

$$HCO_3^- \rightarrow CO_2 + OH^-$$

or $$(COO^-)_2 \rightarrow 2CO_2 + O_2 + 2e^-$$

With above scheme, nanometer $CO_2$ particles are produced; then, the $CO_2$ produced during decomposition of carboxylic acid (e.g., oxalic acid) grows on the existing $CO_2$ nanometer particles (nuclei) into $CO_2$ bubbles.

With above scheme, the oxalic acid added later and the oxalic acid in the oxalic acid aqueous solution in oxidation field state resulted from electrolysis react with the $CO_2$ bubbles, so that a great deal of micro carbonic acid gas bubbles are produced instantaneously.

For the carbonated water described in the present invention, if the first aqueous solution is an aqueous solution with carboxylic acid dissolved, micro carbonic acid gas bubbles can produced by electrolyzing the first aqueous solution; then, the carbonic acid gas bubbles produced in decomposition of carboxylic acid (e.g., oxalic acid) grow on said micro carbonic acid gas bubbles (nuclei), so as to obtain the unique effect of carbonated spring.

If the first aqueous solution is an aqueous solution with carboxylic acid and monovalent cations thereof dissolved in it, said aqueous solution itself serves as buffer solution; therefore, even if the first aqueous solution is electrolyzed, the pH value will not move to the strong alkaline range; as the result, the neutral carbonated water can deliver the unique effect of numerous water bubbles on skin surface and ruddy skin, and facilitate the increase and dilatation of capillary bed, and improved blood circulation in skin.

If the first aqueous solution is an aqueous solution comprising any one of acidic fruit juice or extract of tea as the major component, it can be used to produce the carbonated water described above, which is a carbonated water friendly to the environment and safe to human body.

In addition, the carboxylic acid is preferably at least one selected from oxalic acid, acetic acid, citric acid, succinic acid, malonic acid, fumaric acid, lactic acid, malic acid, and tartaric acid, so that the carbonated water is safe to the environment and human body.

Furthermore, if the carboxylic acid dissolved in the second aqueous solution is oxalic acid, citric acid, malic acid, or tartaric acid contained in any one of acerbic fruit juice or the extract of tea, the second aqueous solution is identical to the first aqueous solution, and the carbonated water is safe to the environment and human body.

If the first aqueous solution is the aqueous solution of potassium oxalate, the aqueous solution of potassium oxalate filled in the electrolytic cell to produce carbonic acid gas, hydrogen and oxygen; after the carbonic acid gas and oxygen are dissolved in the aqueous solution of potassium oxalate, the aqueous solution of oxalic acid is added into the aqueous solution of potassium oxalate, and thereby a carbonated water having the aqueous solution of oxalic acid dissolved with micro carbonic acid gas bubbles as the major component is obtained; said carbonated water can delivery the unique effect of carbonated spring (numerous water vapor bubbles on skin and ruddy skin), and can facilitate the capillary bed to increase and dilate, so as to improve skin blood circulation.

In the carbonated water produced in above embodiment, the concentration of carbonated water is $\geqq 400$ ppm; therefore, the carbonated water can deliver unique feature of carbonated spring (i.e., numerous water bubbles on skin surface and ruddy skin), and can facilitate the increase and dilatation of capillary bed and improved blood circulation in skin.

Hereunder the invention will be further detailed in the examples; however, the invention is not intended to be limited to those examples.

Example 1

As an experiment for producing carbonic acid gas solution as described above, the apparatus shown in FIG. 2 was utilized; 500 ml raw aqueous solution containing 2M potassium oxalate ($K_2C_2O_4$) was filled in an electrolytic cell 2. An ultrasonic generator 4 (Manufactured by TOMY SEIKO CO., LTD., UD-200) was utilized to produce ultrasonic wave, and at the same time, the aqueous solution is electrolyzed for 30 with the electrolytic device 3, in the case that the current was set to 4.5 A and the voltage was set to 0.18V.

The pH value in the electrolyzed aqueous solution of potassium oxalate was measured as 8.75.

Next, an aqueous solution of oxalic acid with pH=4.9 was added into the electrolyzed aqueous solution of potassium oxalate (raw aqueous solution). The pH value in said aqueous solution of oxalic acid was adjusted with potassium hydroxide (KOH) in advance.

The pH value in the raw aqueous solution was measured while the aqueous solution of oxalic acid was added; and the addition of the aqueous solution of oxalic acid was stopped when the pH value in the raw aqueous solution reached to 6.7.

The raw aqueous solution was strongly alkaline initially; as the aqueous solution of oxalic acid was added, the raw aqueous solution was neutralized through the following reaction, and thereby a great deal of micro carbonic acid gas bubbles were produced instantaneously.

$$(COOH)_2 + O_2 + H_2 \rightarrow 2CO_2 + 2H_2O$$

When the raw aqueous solution became weak acidic, the addition of the aqueous solution of oxalic acid was stopped; therefore, a carbonic acid gas solution with a great deal of micro carbonic acid gas bubbles dissolved and mild to human body skin was obtained.

In the carbonated water produced as above, the oxygen and hydrogen produced in electrolysis reacted with the oxalic acid in the aqueous solution of oxalic acid and produced a great deal of micro carbonic acid gas bubbles instantaneously; said carbonic acid gas bubbles were dissolved in the aqueous solution; as a result, when the hands dipped into the aqueous solution of oxalic acid with above micro carbonic acid gas bubbles dissolved, the unique effect of numerous water vapor bubbles on hand skin and ruddy skin could be obtained.

In this example, when producing the carbonic acid gas solution with micro carbonic acid gas bubbles dissolved, the method did not need gas dissipation device, carbonic acid gas bomb, gas separator, or compressor that were required in the method for producing carbonated spring in the prior art. Therefore, the apparatus could easily produce carbonic acid gas solution with dissolved micro carbonic acid gas bubbles at a low cost.

In addition, since the oxalic acid ion in the aqueous solution was ionized in advance; carbonic acid gas solution could be produced in a shorter time.

Figure 6:
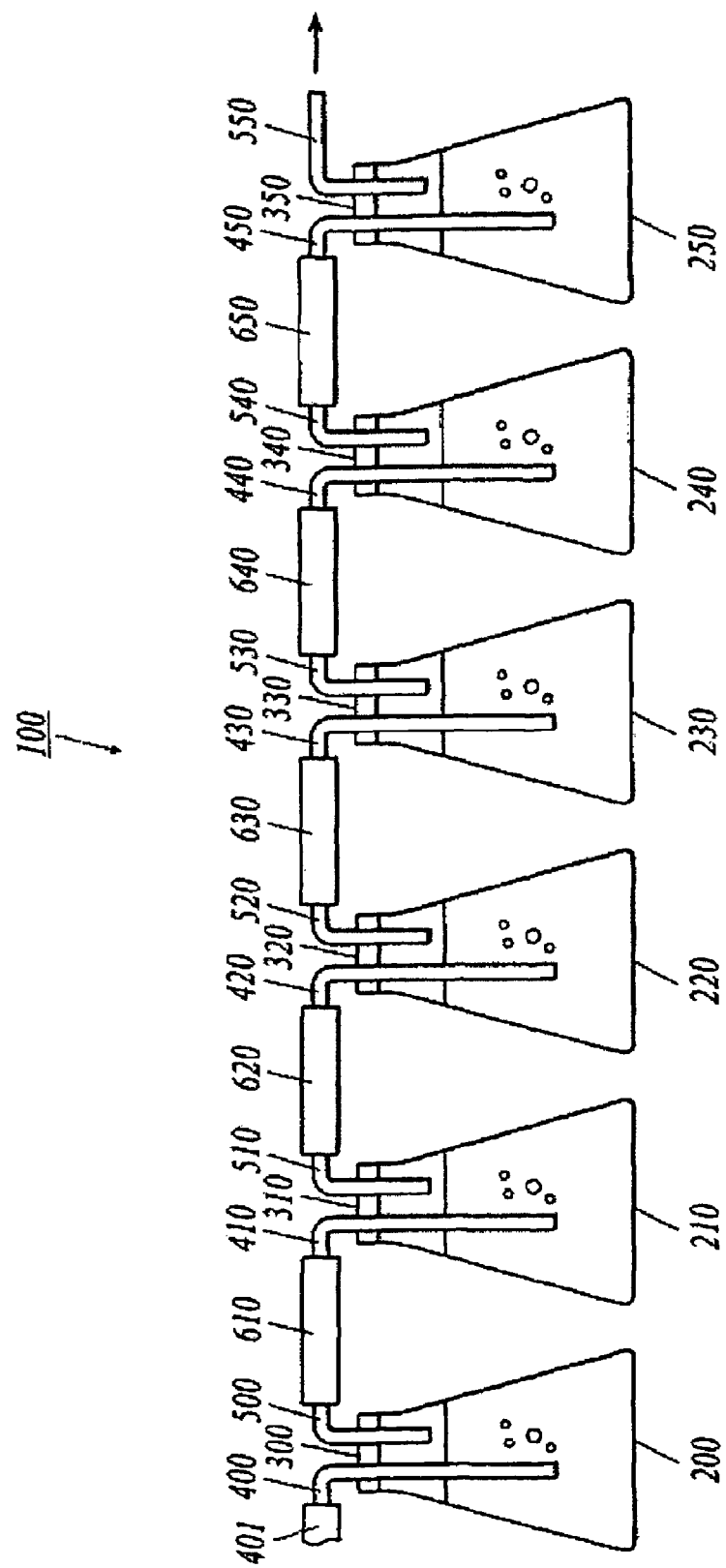
FIG. 6 is a schematic view of the structure of the measuring device for the carbonic acid gas concentration.

The concentration of carbonic acid gas solution produced in that way was measured quantitatively with the measuring device shown in FIG. 6; wherein, the measurement was carried out by measuring the turbidity in the solution resulted from the reaction of calcium hydroxide with carbonic acid gas.

As shown in FIG. 6, the measuring device 100 comprised: a container 200 filled with the carbonated water having micro carbonic acid gas bubbles dispersed in it to be measured, and 5 containers filled with saturated aqueous solution of calcium hydroxide (the first carbonic acid gas absorption container 210, the second carbonic acid gas absorption container 220, the third carbonic acid gas absorption container 230, the fourth carbonic acid gas absorption container 240, and the fifth carbonic acid gas absorption container 250).

The solution to be measured was prepared with 2M potassium oxalate as described above.

The containers had covers (300, 310, 320, 330, 340, and 350) and two pipes were inserted through each cover (400, 410, 420, 430, 440, 450, 500, 510, 520, 530, 540, and 550). Wherein, one pipe was the inlet pipe (400, 410, 420, 430, 440, and 450), and inserted through the cover (300, 310, 320, 330, 340, and 350) below the liquid level of the solution to be measured; the other pipe was the outlet pipe (500, 510, 520, 530, 540, and 550), and inserted through the cover (300, 310, 320, 330, 340, and 350) above the liquid level of the solution to be measured.

The inlet pipe 400 was covered with a cap 401, to prevent intrusion of external air; the top part of outlet pipe 500 was connected to the top part of inlet pipe 410 via the first connecting pipe 610; similarly, the top part of outlet pipe 510 was connected to the top part of inlet pipe 420 via the second connecting pipe 620; that is to say, the top part of each outlet pipe (520, 530, 540, and 550) was connected to the top part of the corresponding inlet pipe (420, 430, 440, and 450) via a connecting pipe (620, 630, 640, and 650). The top part of outlet pipe 550 was connected to a vacuum pump.

Hereunder the method for calculating the total amount of carbon dioxide in the measured object will be described.

As the air in the carbonic acid gas absorption containers (210, 220, 230, 240, and 250) was extracted by the vacuum pump, the pressure in the carbonic acid gas absorption containers (210, 220, 230, 240, and 250) was reduced; as a result, the carbonic acid gas flowed from the container 200 containing the measured solution into the carbonic acid gas absorption containers (210, 220, 230, 240, and 250) in sequence through the inlet pipes (410, 420, 430, 440, and 450) and the outlet pipes (510, 520, 530, 540, and 550).

The carbonic acid gas released above the liquid level of the measured solution flowed into the carbonic acid gas absorption container 210 through the outlet pipe 500, the first connecting pipe 610, and inlet pipe 410, so that the carbonic acid gas bubbles flowed into the saturated aqueous solution of calcium hydroxide through the bottom of inlet pipe 410. As a result, carbonic acid gas was partially absorbed in the aqueous solution of calcium hydroxide and produces calcium carbonate, making the saturated aqueous solution of calcium hydroxide turbid.

The carbonic acid gas that was not absorbed in the saturated aqueous solution of calcium hydroxide in carbonic acid gas absorption container 210 escaped above the liquid level of said saturated aqueous solution of calcium hydroxide, and then flowed into the second carbonic acid gas absorption container through the outlet pipe 510, the second connecting pipe 620, and inlet pipe 420. In the same way, the carbonic acid gas was absorbed in the saturated aqueous solution of calcium hydroxide in carbonic acid gas absorption containers (230, 240, and 250) subsequently, and made the saturated calcium hydroxide aqueous solution turbid.

Next, the turbidity values in the saturated aqueous solutions of calcium hydroxide in carbonic acid gas absorption containers (210, 220, 230, 240, and 250) were measured, and the corrected turbidity values were calculated; then, the concentrations corresponding to the turbidity values were calculated with the standard curve of concentration vs. turbidity obtained from aqueous solutions of sodium carbonate having known concentrations, and the concentration of total carbonic acid gas was obtained.

Here, the standard curve is worked out as follows.

<A> Production of Standard Curve

The standard curve was worked out with aqueous solutions of sodium carbonate having known concentrations. In addition, the turbidity values were calculated by a transmitted light measurement method.

(A1) Preparation of the Aqueous Solution of Sodium Carbonate

Degasified distilled water without dissolved carbon dioxide was added to 1.036 g dry sodium carbonate from Pharmacopeia of Japan to obtain 1 L solution, i.e., 1036 ppm aqueous solution of sodium carbonate. Since the molecular weight of $Na_2CO_3$ is 106 and the molecular weight of $CO_2$ is 44, the $CO_2$ concentration in 1036 ppm aqueous solution of sodium carbonate is 1036×44/106=430.0 ppm.

(A2) Preparation of Aqueous Solution of Calcium Hydroxide

Degasified distilled water without dissolved carbon dioxide was added into 3 g calcium hydroxide from Pharmacopeia of Japan to obtain 1 L solution; in addition, to prevent carbon dioxide in air from being dissolved in the solution, the solution was shaken in an enclosed container for 1 h and then kept still, to obtain calcium hydroxide. Since the molecular weight of $Ca(OH)_2$ is 76, the concentration of the aqueous solution of calcium hydroxide was 0.04 mol/L.

(A3) Measurement of Absorbance 0.1 ml, 0.2 ml, 0.3 ml, 0.4 ml, 0.5 ml, 0.6 ml, and 0.7 ml aqueous solutions of sodium carbonate prepared in (A1) were added into 4.0 ml aqueous solution of calcium hydroxide prepared in (A2), respectively, and the absorbance of the turbid aqueous solutions was measured (at 450 nm).

(A4) Calculation of $CO_2$ Concentration

The $CO_2$ concentrations in the solutions were calculated as follows:

430×0.1/(0.1+4.0)=10.49 ppm, 430×0.2/(0.2+4.0)=20.48 ppm, 430×0.3/(0.3+4.0)=30.00 ppm, 430×0.4/(0.4+4.0) =39.09 ppm, 430×0.5/(0.5+4.0)=47.78 ppm, 430×0.6/ (0.6+4.0)=56.09 ppm, 430×0.7/(0.7+4.0)=64.04 ppm.

(A5) Calculation of Turbidity

Due to the fact that the absorbance (at 450 nm) of 1 ppm standard pottery clay solution (1° turbidity) is 0.434, the turbidity is calculated by multiplying the absorbance measured in (A3) with 2.303 (=1÷0.434).

Figure 7:
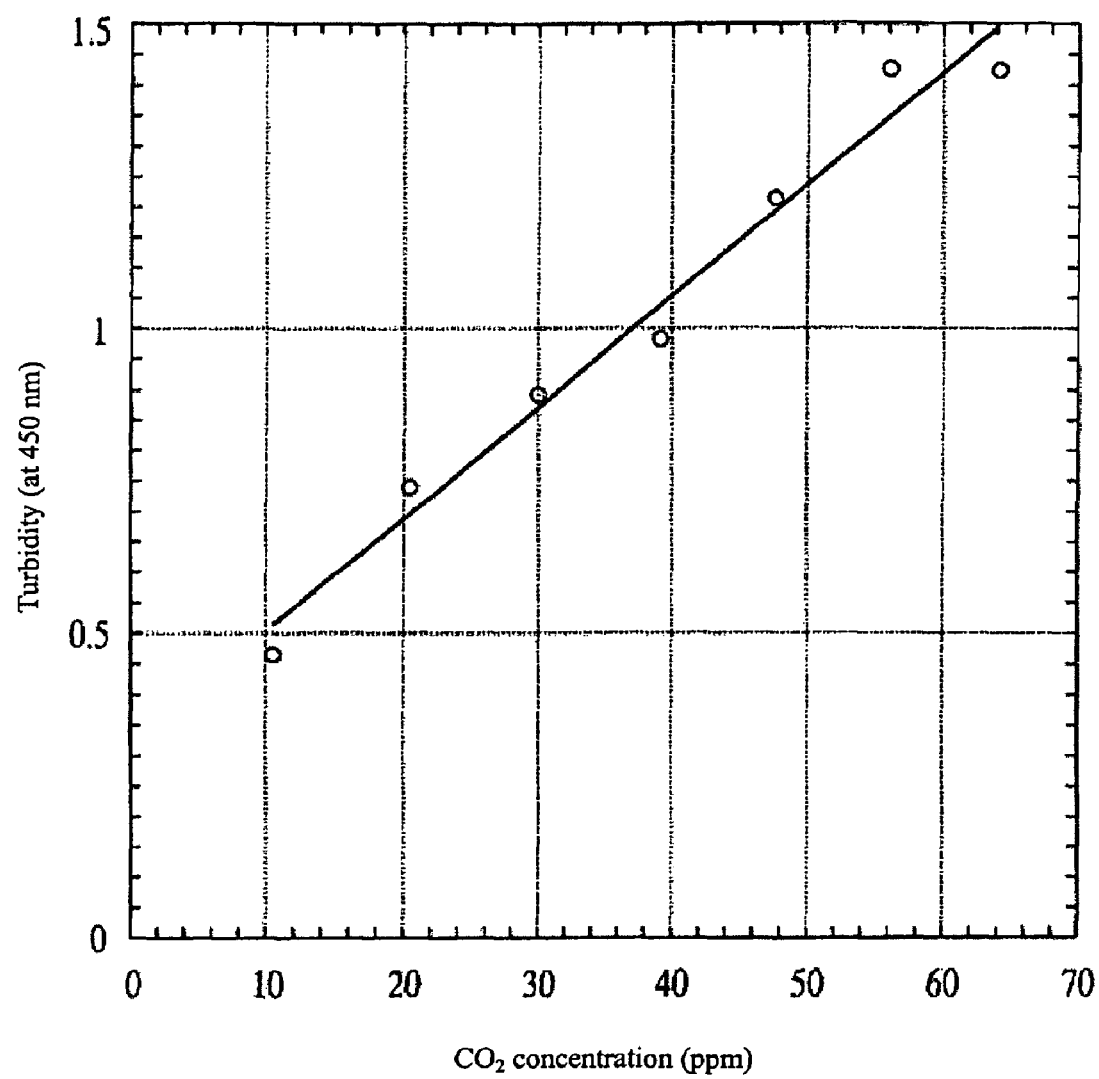
FIG. 7 is a diagram plotted with carbon dioxide concentration as X-axis and absorbance as Y-axis.

The standard curve was plotted with $CO_2$ concentration as X-axis and turbidity as Y-axis (FIG. 7). The obtained formula of calibration line was as follows (wherein, the correlation coefficient is 0.988).

$$y=0.018316x+0.00049 \qquad (3)$$

(A6) Calculation of Corrected Turbidity

The y-intercept (0.00049) in formula (3) was subtracted from turbidity value, to obtain the corrected turbidity value.

Therefore, when the diagram is plotted with $CO_2$ concentration as X-axis and corrected turbidity as Y-axis, the approximation of first degree is as follows:

$$y = 0.018316x \quad (4)$$

The values of measured absorbance, calculated $CO_2$ concentration, turbidity, and corrected turbidity of different aqueous solutions were shown in Table 1.

TABLE 1

| Amount of raw solution | $CO_2$ concentration | Absorbance | Turbidity | Corrected Turbidity |
|---|---|---|---|---|
| 0.1 | 10.49 | 0.204 | 0.470 | 0.1465 |
| 0.2 | 20.48 | 0.323 | 0.744 | 0.4205 |
| 0.3 | 30.00 | 0.389 | 0.896 | 0.5725 |
| 0.4 | 39.09 | 0.429 | 0.988 | 0.6645 |
| 0.5 | 47.78 | 0.529 | 1.218 | 0.8945 |
| 0.6 | 56.09 | 0.620 | 1.428 | 1.1045 |
| 0.7 | 64.04 | 0.619 | 1.426 | 1.1025 |

It could be seen from formulae (3) and (4): the correlation value between $CO_2$ concentration and turbidity or corrected turbidity is high. Therefore, by mixing calcium hydroxide solution into an aqueous solution having unknown $CO_2$ concentration and measuring the absorbance, and then calculating turbidity, the approximate $CO_2$ concentration could be calculated from turbidity.

In the experiment, the amount of raw solution produced from measured aqueous solution of potassium oxalate was 154.61 ml. The $CO_2$ concentration was measured with above measuring device 100 by using the raw solution.

The result was shown in Table 2. Table 2 showed the absorbance at 450 nm, correct turbidity, $CO_2$ concentration (ppm), and $CO_2$ concentration (mg) in raw solution.

In Table 2, the total amount of carbonic acid gas was the sum of carbonic acid gas in all reagents, i.e., 2295 mg.

The 2295 mg carbonic acid gas was dissolved in 154.61 mg raw solution; therefore, $CO_2 = 2295/154.61 = 14844$ ppm; the concentration of carbonic acid in the carbonated water produced in this experiment was determined as 14844 ppm.

TABLE 2

| Carbonic acid gas absorption | Absorbance | Corrected Turbidity | $CO_2$ concentration (ppm) | $CO_2$ concentration in raw solution (mg) |
|---|---|---|---|---|
| Container 1 (210) | 0.999 | 140.342 | 7664 | 1150 |
| Container 2 (220) | 0.453 | 63.64 | 3475 | 521 |
| Container 3 (230) | 0.229 | 32.17 | 1757 | 264 |
| Container 4 (240) | 0.223 | 31.33 | 1711 | 257 |
| Container 5 (250) | 0.134 | 18.82 | 1028 | 103 |

Example 2

As an experiment for producing the carbonic acid gas solution as described above, 500 mg raw aqueous solution containing 2M potassium oxalate ($KHC_2O_4$) was filled into electrolytic cell 2, and was electrolyzed for 30 min by using the electrolytic device without applying ultrasonic wave. The current was set to 4.5 A, and the voltage was set to 0.18V.

The pH value in the electrolyzed aqueous solution of potassium oxalate was measured as 9.25.

Next, aqueous solution of oxalic acid with pH=4.9 was added into the electrolyzed aqueous solution of potassium oxalate (raw aqueous solution). The pH value in said aqueous solution of oxalic acid was adjusted with potassium hydroxide (KOH) in advanced.

The pH value in the raw aqueous solution was measured while the aqueous solution of oxalic acid was added; the addition of aqueous solution of oxalic acid was stopped when the pH value in the raw aqueous solution became 6.5.

The raw aqueous solution was strongly alkaline initially; as the aqueous solution of oxalic acid was added and the raw aqueous solution was neutralized through the following reaction, a great deal of micro carbonic acid gas bubbles were produced instantaneously.

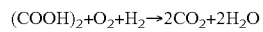

$$(COOH)_2 + O_2 + H_2 \rightarrow 2CO_2 + 2H_2O$$

When the raw aqueous solution became weak acidic, the addition of aqueous solution of oxalic acid was stopped; therefore, a carbonic acid gas solution with a great deal of micro carbonic acid gas bubbles dissolved and mild to human body skin was obtained. After the hand was dipped into the carbonated water having an aqueous solution of oxalic acid dissolved with carbonic acid gas bubbles as the major component produced by above method for 5 min, and then it was found that the effect was identical to that in the case in which ultrasonic wave was applied, i.e., the unique effect of numerous water bubbles on skin surface and ruddy skin was obtained.

Example 3

Above experiment for producing carbonic acid gas solution was carried out by using low concentration potassium oxalate ($K_2C_2O_4$).

First, 500 ml raw aqueous solution containing 0.3M potassium oxalate ($KHC_2O_4$) was filled into electrolytic cell 2, and was electrolyzed for 30 min by using the electrolytic device 3 and applying ultrasonic wave continuously. The current was set to 4.38 A, and the voltage was set to 2.3V.

25 ml aqueous solution of oxalic acid was added into the aqueous solution of potassium oxalate produced as above.

After the hand was dipped into the carbonated water having an aqueous solution of oxalic acid dissolved with carbonic acid gas bubbles as the major component produced by above method for 5 min, and then it was found that the effect was identical to that in the case in which ultrasonic wave was applied, i.e., the unique effect of numerous water bubbles on skin surface and ruddy skin was obtained.

Example 4

In 500 ml raw aqueous solution containing 0.3M potassium oxalate ($K_2C_2O_4$), the 0.3M potassium oxalate was replaced with 0.2M and 0.1M potassium oxalate respectively and the experiment was carried out to produce corresponding aqueous solutions of potassium oxalate. The hand was dipped in the aqueous solution of oxalic acid produced in that way for 5 min, and then the unique effect of numerous water bubbles on skin surface and ruddy skin was found.

However, when the concentration of potassium oxalate was relatively low, it was found that the bubbles attached to the skin slowly and mildly.

Therefore, above carbonated water could facilitate the capillary bed to grow and dilate, and could improve the skin blood circulation.

Example 5

1M sodium citrate (pH=8.1), 1M citric acid (pH=0.8), and 1M sodium bicarbonate were used as the raw solution, respectively. 200 ml sodium citrate was taken and prepared into 800 ml aqueous solution of sodium citrate (pH=8.0) by using water.

Citric acid was added into that aqueous solution, and the change of pH value in the solution was observed. The obtained result was shown in the following table.

TABLE 3

| | Total amount of citric acid (ml) | | | | | |
|---|---|---|---|---|---|---|
| | 4 | 8 | 12 | 16 | 20 | 28 |
| pH | 7.0 | 7.0 | 7.0 | 7.0 | 7.0 | 7.0 |

100 ml sodium bicarbonate (0.1M) was added into that solution to produce 1 L mixed solution, and the mixed solution was filled into the electrolytic cell 2 as the first aqueous solution and electrolyzed with the electrolytic device 3.

As the solution was electrolyzed, bubbles occurred slowly around the electrode.

The current was set to 4.98 A, the voltage was set to 2.8V, and the electrolysis time was 1 h.

The result was: the pH value in the aqueous solution was 7.0.

The pH value did not change during the electrolysis because of the effect of buffer solution.

When 20 ml 1M oxalic acid was added into the electrolyzed aqueous solution, micro bubbles began to attach to the hands and makes the hands ruddy slowly.

In addition, the pH value was kept at 7.0, without any change.

Figure 8:
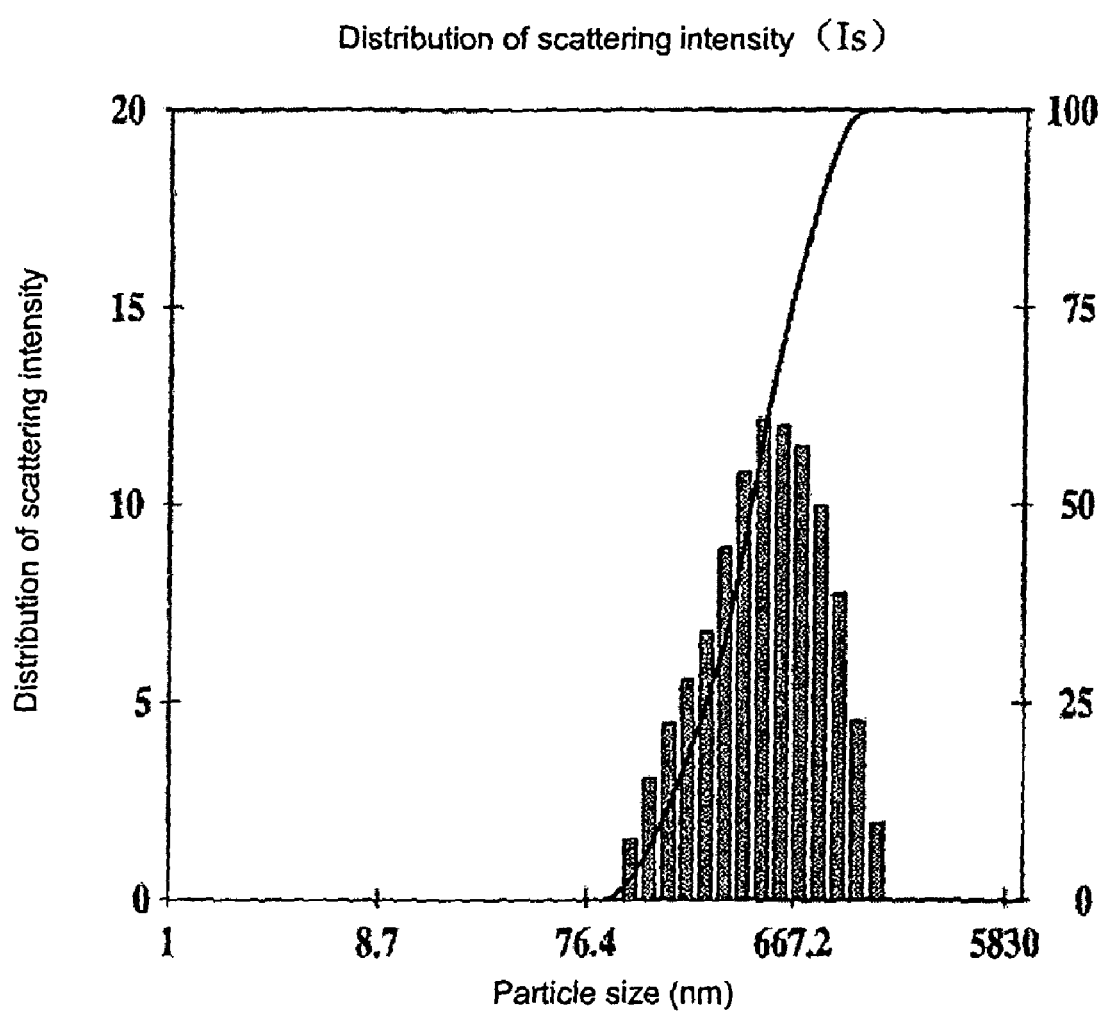
FIG. 8 is a diagram indicating the particle size of carbonic acid gas in the carbonated water produced with the method in the present invention.

The mean particle size of micro carbonic acid gas bubbles in the produced carbonic acid gas solution was measured as 405.1 nm (see FIG. 8).

In above particle size measurement, a quasi-elastic light scattering photometer (from Otsuka Electronics Co., Ltd., Model No.: ELS-8000) was used.

For the purpose of comparison, the particle size of micro carbonic acid gas bubbles in carbonated spring containing 1000 ppm carbonic acid gas was measured. The mean particle size was measured as 6563.0 nm (see FIG. 9). Above carbonated spring was produced with the carbonated spring producing apparatus (C. C. Carbo) from Mitsubishi Rayon Co., Ltd.

Figure 9:
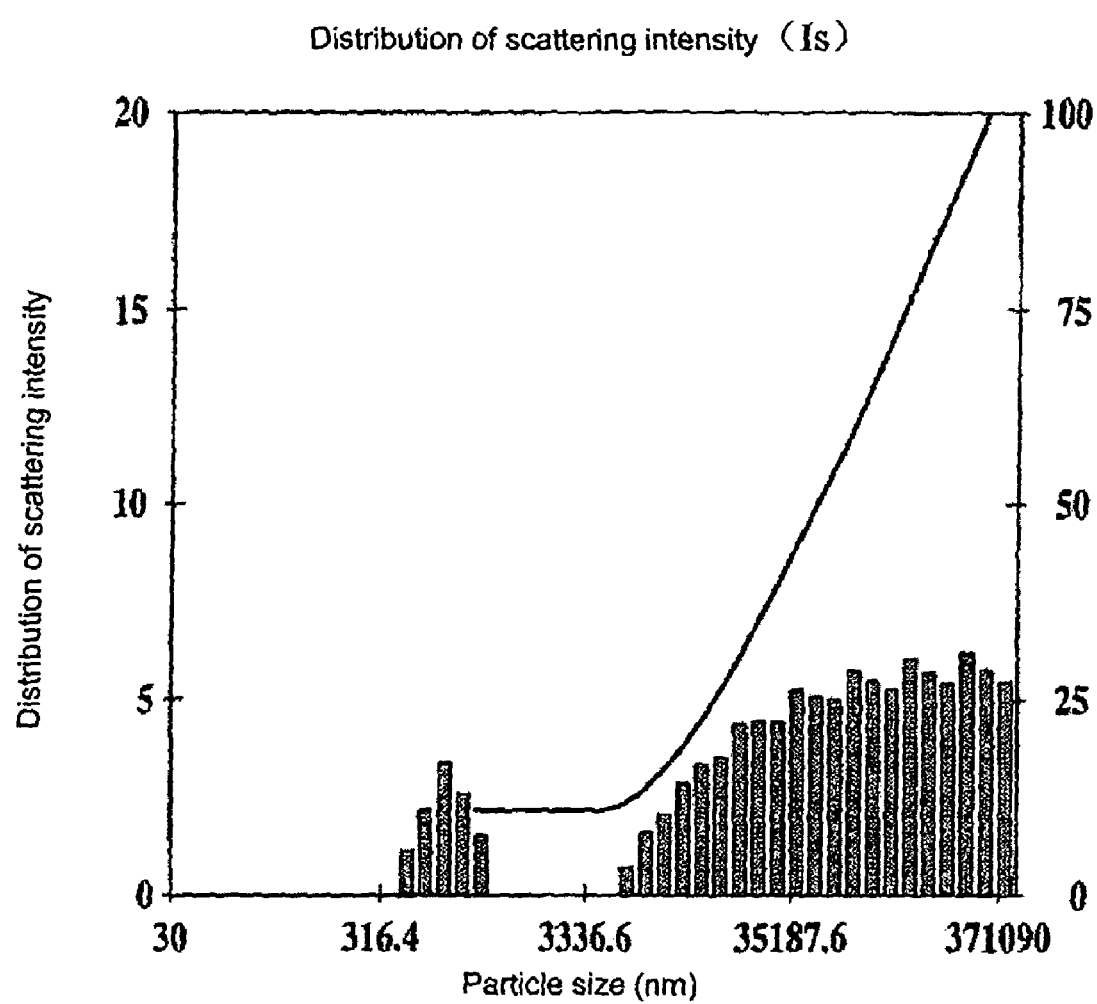
FIG. 9 is a diagram indicating the particle size of carbonic acid gas in the carbonated water produced with carbonic acid gas bomb in the prior art.

It could be seen from FIG. 8 and FIG. 9: in the carbonic acid gas produced in this example, the distribution of scattering intensity was almost at one peak, i.e., only carbonic acid gas having mean particle size was produced. However, in the carbonic acid gas solution produced with the carbonated spring producing apparatuses in the prior art, the scattering intensity was distributed at two peaks, which meant a great deal of carbonic acid gas having a larger particle size was produced.

Example 6

An aqueous solution (pH=5.9) was prepared with 10 ml citric acid (0.01M) and 100 ml sodium citrate (0.1M), and 300 ml sodium bicarbonate (0.3M) was added thereto, to obtain the first aqueous solution.

The pH value was 7.02.

The first aqueous solution produced as above was added into electrolytic cell 2, and electrolyzed directly with the electrolytic device 3.

The current was set to 4.98 A, and the voltage was set to 2.8V.

After 1 h electrolysis, the pH value was measured as 8.70.

When 20 ml 1M oxalic acid as the second aqueous solution was added into the electrolyzed first aqueous solution, a great deal of bubbles occurred; after the hand was dipped into said aqueous solution, a great deal of bubbles attached to the hand and the hand became ruddy.

At that time, the pH value was 7.0.

Example 7

10 ml citric acid (0.01M) was added into 100 ml sodium citrate (0.1M) (the resulting pH=7.0), and 200 ml 0.05M acetic acid buffer solution was added thereto. And then, water was added to produce 700 ml solution as the first aqueous solution. Now, the pH value was 5.6.

300 ml sodium bicarbonate (0.3M) was added into the first aqueous solution, and then the resulting solution was filled into electrolytic cell 2 and electrolyzed with the electrolytic device 3.

Before the electrolysis began, the pH value in the first aqueous solution was 6.9. The current was set to 4.98 A, and the voltage was set to 2.7V. The electrolysis time was 1 h.

After the electrolysis, the pH value in the first aqueous solution was 8.77.

The electrolyzed first aqueous solution was alkaline. 30 ml 1M oxalic acid as the second aqueous solution was added into the electrolyzed first aqueous solution (1 L), and at that time the pH value was reduced to 7.0.

After the hand was dipped into said aqueous solution, a great deal of bubbles attached to the hand and the hand became ruddy.

Example 8

40 ml 0.04M citric acid was added into 200 ml 0.2M sodium citrate (the resulting pH=5.5) to produce the first aqueous solution; 300 ml 0.3M sodium bicarbonate was added thereto; then the mixed aqueous solution was filled into the electrolytic cell 2.

Before the electrolysis began, the pH value was 5.8.

The current was set to 5 A, and the voltage was set to 2.8V. The electrolysis time was 1 h. After 1 h, the pH value was 8.7; citric acid was added to adjust the pH value to 6.5, and then, extract of tea as the second aqueous solution was added.

The extract of tea was prepared as follows: 7 L distilled water was added to 150 g commercial Shizuoka Sencha Tea, cooked for 5 min, cooled naturally to about 40□, filtered with filter paper, and condensed in an evaporator at 80□ to obtain the extract of tea.

When the extract of tea was added, the aqueous solution turns into brown color; after the hand was dipped into the aqueous solution, a great deal of bubbles attached to the hand and the hand became ruddy.

Example 9

900 ml water was added into 100 ml commercial fruit juice (Trade name: CC Lemon) (the resulting pH=3.6) to produce the first aqueous solution; 100 ml 0.1M sodium bicarbonate was added into the first aqueous solution; the mixed solution was filled into electrolytic cell 2, and electrolyzed with electrolytic device 3 for 30 min.

The current was set to 5 A; the voltage was set to 4V; the pH value in the electrolyzed aqueous solution was 8.7.

The electrolyzed first aqueous solution was alkaline; 8 ml 1M oxalic acid was added into the electrolyzed aqueous solution (500 ml), to adjust the pH value to 6.6. Next, 8 ml 1M citric acid was added into the aqueous solution; the final pH value was 6.3. After the hand was dipped into said aqueous solution, a great deal of bubbles attached to the hand and the hand became ruddy.

Under the same conditions, the extract of tea described in example 8 was used to replace the 8 ml 1M citric acid; after the hand was dipped into the aqueous solution, a great deal of bubbles attached to the hand and the hand became ruddy.

Example 10

Figure 5:
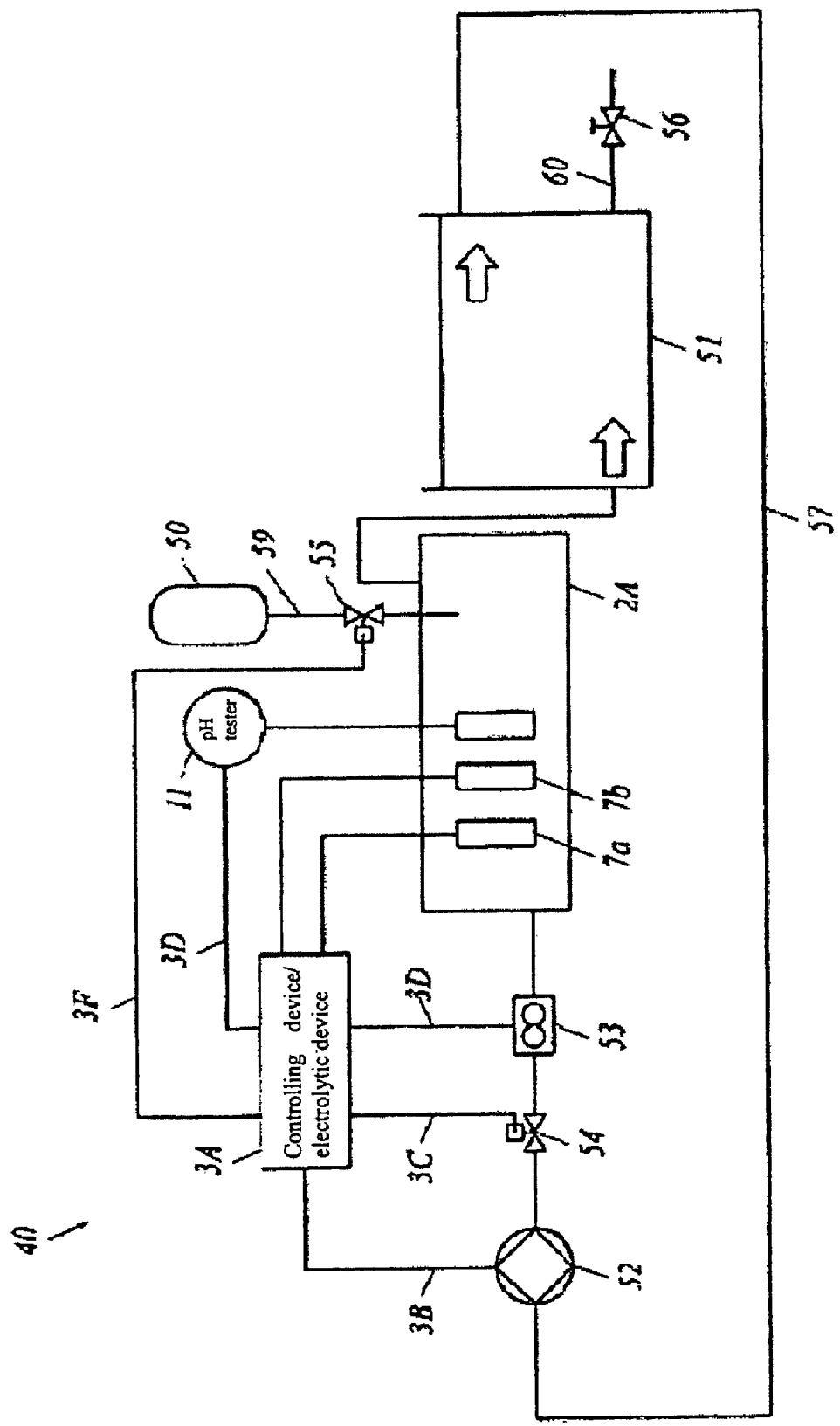
FIG. 5 is a diagram of the structure of the apparatus for producing carbonic acid gas solution in another embodiment in the present invention.

The apparatus shown in FIG. 5 was used, and a bath vessel was used as the reaction vessel 51, to check whether the expected carbonated spring could be obtained. 12 bottles (about 10 L) of lemon solution (Trade name: キレートレモン) were prepared as the first aqueous solution, and diluted with 150 L tub water. In view that the citric acid in above lemon solution may be not enough, 110 g citric acid was added, to adjust the final aqueous solution in the reaction vessel 51 to about 0.005M.

1 L 1M sodium bicarbonate was dissolved into the aqueous solution; the circulating pump 52 was started to circulate about 160 L aqueous solution; at the same time, the electrolytic device 3A was started to apply current to the electrodes 7a and 7b in the electrolytic cell 2A to electrolyze the solution.

The current was set to 5 A, and the voltage was set to 2.8V Electrolysis was carried out for 30 min with a constant current of 5 A.

In addition, 20 L water flowed through the circulating pump per 1 min. The water temperature was 30□; after 30 min, 5 bottles of lemon solution (Trade name: キレートレモン) were added into the electrolyzed aqueous solution, and 1M citric acid was further added appropriately; now, the body was immersed into the aqueous solution; bubbles began to attach to the body skin slowly; after 30 min bath, the body color changed, i.e., the body part immersed in the water became ruddy.

Example 11

200 ml 0.2M succinic acid was added into 500 ml 0.5M sodium succinate to produce the first aqueous solution; 300 ml 0.3M sodium bicarbonate was added into the aqueous solution, and the mixed solution was filled into electrolytic cell 2 and was electrolyzed with the electrolytic device 3.

The current was set to 5 A, and the voltage was set to 3.16V. The electrolysis was carried out for 30 min.

Next, 2 ml 1M oxalic acid was added into 100 ml electrolyzed aqueous solution; after the hand was dipped into the aqueous solution, a great deal of bubbles attached to the hand and the hand became ruddy.

In the present invention, in an electrolytic cell with electrodes, the first aqueous solution is electrolyzed by applying DC voltage between the electrodes, to form an oxidation field short of electrons in the aqueous solution, and the second aqueous solution with carboxylic acid dissolved is mixed into the first aqueous solution in oxidation field state, so that the first aqueous solution in oxidation field state obtains electrons and is deoxidized, and the carboxylic acid is oxidized, to produce carbonic acid gas in the aqueous solution. Therefore, in the present invention carbonic acid gas solution with micro bubbles dissolved can be produced at a low cost easily, without emitting unwanted carbonic acid gas to the atmosphere, i.e., environmentally friendly. Such an apparatus for producing carbonic acid gas solution does not need the gas dissociation device, carbonic acid gas bomb, gas separator, or compressor, etc., which are required in the method for producing carbonated spring in the prior art.

The carbonated water having aqueous solution dissolved with the micro carbonic acid gas bubbles produced with above method as the major component can deliver the unique effect of carbonated spring (i.e., numerous water bubbles on skin surface and ruddy skin), and can facilitate increase and dilatation of capillary bed and improve blood circulation in skin, because it contains a great deal of nanometer-level carbonic acid gas bubbles.

What we claim is:

1. A method for producing a carbonic acid gas solution comprising electrolyzing, in an electrolytic cell with electrodes, a first aqueous solution to a pH value of 6 or higher by applying a DC voltage between the electrodes, to form an oxidation field state short of electrons in the aqueous solution; and mixing a second aqueous solution with a carboxylic acid dissolved therein into the first aqueous solution in the oxidation field state, so that the first aqueous solution in the oxidation field state obtains electrons and is deoxidized, and the carboxylic acid is oxidized, to produce carbonic acid gas,
wherein, after the first aqueous solution is electrolyzed to a pH value of 6 or higher, an acidic solution is added thereto to adjust the pH value of the first aqueous solution into a range of 5-7, and then, the second aqueous solution is added thereto to keep the pH value within the range of 5-7.

2. The method for producing carbonic acid gas solution according to claim 1, characterized in that said first aqueous solution is an aqueous solution with a carboxylic acid dissolved therein.

3. The method for producing carbonic acid gas solution according to claim 1, characterized in that said first aqueous solution comprises a carboxylic acid and a monovalent cation salt thereof dissolved therein.

4. The method for producing carbonic acid gas solution according to claim 1, characterized in that said carboxylic acid is at least one selected from oxalic acid, acetic acid, citric acid, succinic acid, malonic acid, fumaric acid, lactic acid, malic acid, and tartaric acid.

5. The method for producing carbonic acid gas solution according to claim 1, characterized in that said first aqueous solution is an aqueous solution comprising any one of acidic fruit juice or extract of tea as the major component.

6. A method for producing a carbonic acid gas solution comprising electrolyzing, in an electrolytic cell with electrodes, a first aqueous solution by applying a DC voltage between the electrodes, to form an oxidation field state short of electrons in the aqueous solution; and mixing a second aqueous solution with a carboxylic acid dissolved therein into the first aqueous solution in the oxidation field state, so that the first aqueous solution in the oxidation field state obtains electrons and is deoxidized, and the carboxylic acid is oxidized, to produce carbonic acid gas, wherein said first aqueous solution is an aqueous solution comprising any one of acidic fruit juice or extract of tea as the major component.

7. The method for producing carbonic acid gas solution according to claim 6, characterized in that said first aqueous solution is an aqueous solution with a carboxylic acid dissolved therein.

8. The method for producing carbonic acid gas solution according to claim 6, characterized in that said first aqueous solution comprises a carboxylic acid and a monovalent cation salt thereof dissolved therein.

9. The method for producing carbonic acid gas solution according to claim 6, characterized in that said carboxylic acid is at least one selected from oxalic acid, acetic acid, citric acid, succinic acid, malonic acid, fumaric acid, lactic acid, malic acid, and tartaric acid.

* * * * *